United States Patent
Yan et al.

(10) Patent No.: US 9,279,117 B2
(45) Date of Patent: Mar. 8, 2016

(54) TRANSGENIC MOUSE CONDITIONALLY EXPRESSING MMP12 FOR STUDYING MYELOPOIESIS, IMMUNITY AND TUMORIGENESIS

(75) Inventors: Cong Yan, Carmel, IN (US); Hong Du, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 181 days.

(21) Appl. No.: 13/353,272

(22) Filed: Jan. 18, 2012

(65) Prior Publication Data

US 2012/0204274 A1    Aug. 9, 2012

Related U.S. Application Data

(60) Provisional application No. 61/433,817, filed on Jan. 18, 2011.

(51) Int. Cl.
*A01K 67/027* (2006.01)
*C12N 9/64* (2006.01)

(52) U.S. Cl.
CPC .......... *C12N 9/6416* (2013.01); *A01K 67/0275* (2013.01); *A01K 2217/052* (2013.01); *A01K 2217/203* (2013.01); *A01K 2217/206* (2013.01); *A01K 2227/105* (2013.01); *A01K 2267/0331* (2013.01); *A01K 2267/0368* (2013.01); *C12Y 304/24065* (2013.01)

(58) Field of Classification Search
USPC ....................................... 800/18, 3
See application file for complete search history.

(56) References Cited

PUBLICATIONS

Ristevski, Molecular Biotechnology, 2005, 29:153-163.*
Gama Sosa et al, Brain Struct Funct, 2009, 214:91-109.*
Smith, Journal of Biotechnology, 2002, 99:1-22.*
Qu et al, Cancer Res, 2009, 69:7252-7261.*
Yan et al, Am J Pathol, 2006, 169:916-926.*
Peng Qu, et al., Matrix metalloproteinase 12 overexpression in myeloid lineage cells plays a key role in modulating myelopoiesis, immune suppression, and lung tumorigenesis, Blood, Mar. 2011, vol. 117, No. 17, pp. 4476-4489.
Peng Qu, et al., Matrix Metalloproteinase 12 Overexpression in Lung Epithelial Cells Plays a Key Role in Emphysema to Lung Bronchioalveolar Adenocarcinoma Transition, Cancer Research, Aug. 2009, vol. 69, No. 18, pp. 7252-7261.

* cited by examiner

*Primary Examiner* — Michael Wilson
(74) *Attorney, Agent, or Firm* — Faegre Baker Daniels LLP

(57) ABSTRACT

A myeloid-specific c-fms-rtTA/(TetO)$_7$-CMV-MMP12 bitransgenic mouse model was created. Induction of MMP12 abnormally elevated frequencies and numbers of common myeloid progenitor (CMP) and granulocyte/macrophage progenitor (GMP) populations, and decreased the frequency and number of the megakaryocyte/erythrocyte progenitor (MEP) population in bone marrow. CD11b$^+$/Gr-1$^+$ immature cell population increased in multiple organs. An immunosuppressive function on T cell proliferation and function by CD11b$^+$/Gr-1$^+$ immature cells was seen in vitro and in vivo from MMP12 over-expression. MMP12 stimulated (Lin$^-$) progenitor cells to differentiate into CD11b$^+$/Gr-1$^+$ immature cells showing immunosuppression on T cell proliferation and function in vitro. Regulatory T cells were increased. In the lung, concentration of interleukin (IL)-6 was increased, which activated oncogenic signal transducer and increased expression of Stat3 downstream genes in epithelial tumor progenitor cells. Spontaneous emphysema and lung adenocarcinoma sequentially developed after MMP12 over-expression. MMP12-induced myeloid cell autonomous defect led to abnormal myelopoiesis, immune suppression and lung adenocarcinoma.

7 Claims, 35 Drawing Sheets

Panel A.

Panel B.

Panel A

Panel B

Panel A

Panel B

Panel A

Panel B

Panel A

Panel B

Panel A

Panel B

Panel C

Panel C

Panel A

Panel B

Panel A

Panel B

Panel A

Panel B

US 9,279,117 B2

TRANSGENIC MOUSE CONDITIONALLY EXPRESSING MMP12 FOR STUDYING MYELOPOIESIS, IMMUNITY AND TUMORIGENESIS

PRIORITY CLAIM

This application claims the benefit of U.S. Provisional Patent Application No. 61/433,817 filed on Jan. 18, 2011 which is incorporated herein by reference in its entirety.

STATEMENT REGARDING FEDERALLY SPONSORED RESEARCH OR DEVELOPMENT

This invention was made with government support under Grant Numbers: HL-061803, HL-067862, CA 138759 and HL087001 awarded by the National Institutes of Health. The United States Government has certain rights in the invention.

BACKGROUND

Smoking-induced lung cancer is the leading death in cancer patients worldwide[22]. Persistent inflammation plays a major role in promoting lung cancer in humans and animals and has also been implicated in a wide variety of diseases from heart conditions to metabolic syndrome. A better understanding of the molecular and cellular mechanisms governing this pathogenic process are integral to developing new therapies to treat and perhaps prevent conditions related to this metabolic state. One class of enzymes that may be involved in diseases such as lung cancer are the zinc-dependent matrix metalloproteinases (MMPs).

Given their possible role in tumorigenesis and perhaps other pathologies, there is a need for better model for determining the tissue specific role that MMPs plays in human and animal pathology. Some aspects of the instant invention provide tools that provide better insights into these processes.

SUMMARY

Matrix metalloproteinase 12 (MMP12) is a macrophage secreting proteinase. In order to fully understand the function of MMP12 in myeloid lineage cells, a myeloid-specific c-fms-rtTA/(TetO)$_7$-CMV-MMP12 bitransgenic mouse model was created. In this bitransgenic system, induction of MMP12 abnormally elevated frequencies and numbers of common myeloid progenitor (CMP) and granulocyte/macrophage progenitor (GMP) populations, and decreased the frequency and number of the megakaryocyte/erythrocyte progenitor (MEP) population in the bone marrow. The CD11b$^+$/Gr-1$^+$ immature cell population was systemically increased in multiple organs. Both in vitro and in vivo studies showed an immunosuppressive function on T cell proliferation and function by CD11b$^+$/Gr-1$^+$ immature cells from MMP12 overexpression bitransgenic mice. MMP12 directly stimulated lineage negative (Lin$^-$) progenitor cells to differentiate into CD11b$^+$/Gr-1$^+$ immature cells that showed immunosuppression on T cell proliferation and function in vitro. Regulatory T cells (Tregs) were increased. In the lung, the concentration of interleukin (IL)-6 was increased, which aberrantly activated oncogenic signal transducer and activator of transcription 3 (Stat3) and increased expression of Stat3 downstream genes in epithelial tumor progenitor cells. Spontaneous emphysema and lung adenocarcinoma were sequentially developed after MMP12 over-expression. Bone marrow chimeras confirmed that the MMP12-induced myeloid cell autonomous defect led to abnormal myelopoiesis, immune suppression and lung adenocarcinoma.

Immature myeloid-originated cells facilitate tumor growth by suppressing immune surveillance. As disclosed herein cells play a roll in the inflammation augmented cancer formation. Elevation of CD11b+/Gr-1+ myeloid-derived suppressor cells (MDSCs) is associated with tumor growth. Since zinc-dependent matrix metalloproteinases (MMPs) act as modulators for inflammation and innate immunity by activating, deactivating or modifying the activities of signaling cytokines, chemokines and receptors through proteolytic and nonproteolytic functions, the aberrant expression of MMPs in myeloid lineage cells may play a critical role in modulating CD11b+/Gr-1+ MDSCs homeostasis and cancer formation.

In the c-fms/rtTA system, the "activator" transgenic mouse line, disclosed herein, bears the reverse tetracycline-responsive transactivator (rtTA) fusion protein under the control of the 7.2-kb 5'-flanking regulatory sequence and the downstream intron 2 of the c-fms gene (designated as c-fms-rtTA mice). The c-fms gene encodes the receptor for macrophage CSF (CSF-1) and is selectively expressed in macrophage lineages. Therefore, the rtTA expression is restricted to macrophages in transgenic mice. In the second transgenic mouse line, the MMP12 gene is under the control of the tetracycline operator (TetO) DNA binding sequence that is linked to a minimal promoter (designated as (TetO)$_7$-CMV-MMP12 mice). After crossbreeding, expression of the MMP12 gene is induced by the addition of doxycyline in bitransgenic mice (designated as c-fms-rtTA/(TetO)$_7$-CMV-MMP12 bitransgenic mice). Some of the uses of this animal system including testing for cancer biomarker diagnosis/prognosis, pharmacological drugs and immunotherapy in treating cancer.

Some embodiments include transgenic animals, comprising: a myeloid specific c-fms-rtTA(TetO)$_7$-CMV-MMP12 construct. In some embodiments the animal is a mouse and in some embodiments the animal is bitransgenic for the vector.

Still other embodiments of the invention include methods for screening for reagents that can be used to treat or diagnose pathologies including those related to immuno-function, inflammation, tumorigenesis and other. These methods comprise the step of contact an animal that is bitransgenic in c-fms-rtTA(TetO)$_7$-CMV-MMP12 with a reagent and then and observing a change in at least a portion of the animal resulting from said contacting step. In some embodiment the reagents are selected from the group including, but not limited to, small molecules, biologics, snRNA and the like. These reagents may include a change in the animal related to the expression, activity, or effect on the animal of matrix metalloproteinase 12 (MMP12).

In some embodiments the reagents may increase the level and or activity of MMP12. In some embodiments the reagent may suppress or otherwise the ability of MMP12 activity to induce a change in the animals tissues and or cells. In some embodiments the reagents may induce a change in the immune system of the animal. In some embodiments they may effect a change in the propensity of the animal to develop a tumor or to exhibit heightened inflammation.

In some embodiment the bitransgenic animals is predominately express MMP12 in myeloid lineage cells. In some embodiments the myeloid lineage cells In some embodiment myeloid specific expression of MMP12 stimulates Lin– progenitor cells to differential into a population of CD11$^+$/Gr-1$^+$ that exhibit elevated levels of Stat3, NFkB p65 and C/EBPα, activation.

Still other embodiments of the invention include methods for modeling diseases or conditions in animals primarily mice, these method include the step of modulating the activity of -fms-rtTA(TetO)$_7$-CMV-MMP12 in a mouse wherein said mouse in bitransgenic for fms-rtTA(TetO)$_7$-CMV-MMP12; and following the progression of at least one pathology related to the activity of said fms-rtTA(TetO)$_7$-CMV-MMP12. In some embodiments the pathology being modeled includes, but is not limited to, at least one of the following conditions emphysema bronchoalveolar adenocarcinoma, immuno-suppression, inflammation and chronic obstructive pulmonary disease.

SEQUENCE LISTING

| | |
|---|---|
| Upstream mCCL5: | 5'-GGAGTATTTCTACACCAGCAGCAA-3' SEQ ID NO. 1. |
| Downwtream mCCL5: | 5'-CGGTTCCTTCGAGTGACAAAC-3' SEQ ID NO. 2. |
| Upstream mCCL8: | 5'-AAAGCTACGAGAGAATCAACAATATCC-3' SEQ ID NO. 3. |
| Downstream mCCL8: | 5'-CCTGCTTGGTCTGGAAAACC-3' SEQ ID NO. 4. |
| Upstream CSF-1: | 5'-TCCAATAACCTGAACAGCTGCTT-3' SEQ ID NO. 5. |
| Downstream CSF-1: | 5'-AGTTCGGACACAGGCCTTGT-3' SEQ ID NO. 6. |
| Upstream mGP130: | 5'-CCCATGGGCAGGAATATAGATC-3' SEQ ID NO. 7. |
| Downstream mGP130: | 5'-TTCCCATTGGCTTCAGAAAGA-3' SEQ ID NO. 8. |
| Upstream mIL-1β: | 5'-TTGACGGACCCCAAAAGATG-3' SEQ ID NO. 9. |
| Downstream mIL-1β: | 5'-CAGGACAGCCCAGGTCAAA-3' SEQ ID NO. 10. |
| Upstream mIL-6: | 5'-GAGGCTTAATTACACATGTTC-3' SEQ ID NO. 11. |
| Downstream mIL-6: | 5'-TGCCATTGCACAACTCTTTTCT-3' SEQ ID NO. 12. |
| Upstream mLif: | 5'-GAGTCCAGCCCATAATGAAGGT-3' SEQ ID NO. 13. |
| Downstream mLif: | 5'-GTGCAGAACCAGCAGCAGTAAG-3' SEQ ID NO. 14. |
| Upstream mMMP-12: | 5'-TGGTATTCAAGGAGATGCACATTT-3' SEQ ID NO. 15. |
| Downstream mMMP-12: | 5'-GGTTTGTGCCTTGAAAACTTTTAGT-3' SEQ ID NO. 16. |
| Upstream mTNFsf9: | 5'-CGCCAAGCTACTGGCTAAAAA-3' SEQ ID NO. 17. |
| Downstream mTNFsf9: | 5'-GGCTGTGCCAGTTCAGAGTTG-3' SEQ ID NO. 18. |
| Upstream mVEGF: | 5'-CCCACGTCAGAGAGCAACATC-3' SEQ ID NO. 19. |
| Downstream mVEGF: | 5'-TGGCTTTGGTGAGGTTTGATC-3' SEQ ID NO. 20. |

DESCRIPTION

Figure 1A:
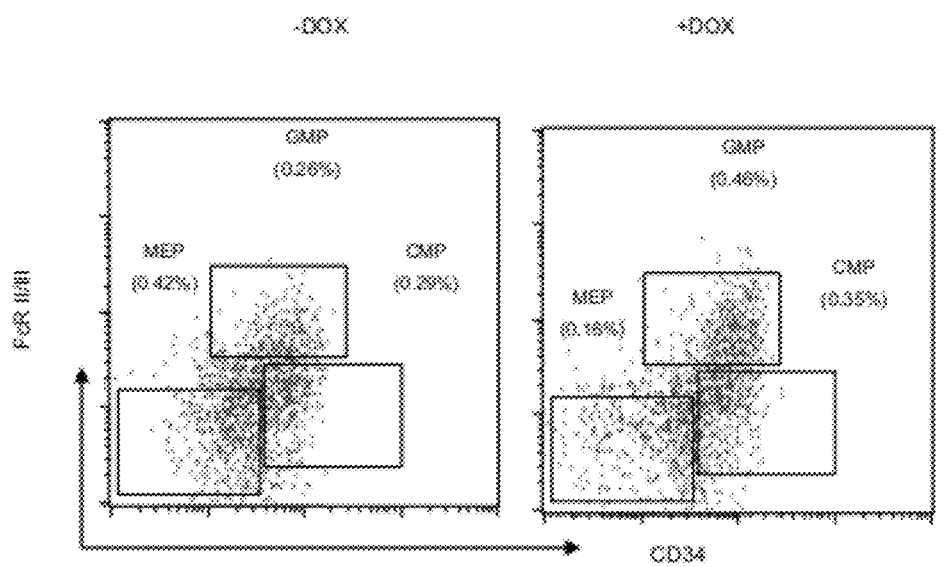
FIG. 1A.—Representative flow cytometry profiles of bone marrow progenitor cell populations.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

In order to elucidate the functional roles of MMP12 in promoting inflammation and initiating tumorigenesis, a myeloid-specific c-fms-rtTA/(TetO)$_7$-CMV-MMP12 bitransgenic mouse model was created under the control of the c-fms promoter/intron 2 as previously reported[12][13]. Both in vivo and in vitro results have shown that MMP12 is a pleiotrophic molecule that plays critical roles in regulating hematopoiesis, myelopoiesis, immune suppression and pulmonary pathogenesis including emphysema and tumorigenesis.

The expression of MMP12 in macrophages is induced in the lung of cigarette smokers. From clinical studies, MMP12 correlates with early cancer-related deaths in non-small cell lung cancer (NSCLC), especially with those associated with tobacco cigarette smoke exposure. Using the bitransgeneic mouse discussed herein it can be demonstrated that MMP12 in myeloid cells plays a critical role in emphysema/chronic obstructive pulmonary disease (COPD) to lung cancer transition.

Inflammation plays a critical role in lung cancer formation. During this process, immature myeloid-originated cells facilitate tumor growth by suppressing immune surveillance[1-3]. Especially, elevation of CD11b+/Gr-1+ myeloid-derived suppressor cells (MDSCs) is associated with tumor growth. Since zinc-dependent matrix metalloproteinases (MMPs) act as modulators for inflammation and innate immunity by activating, deactivating or modifying the activities of signalling cytokines, chemokines and receptors through proteolytic and nonproteolytic functions[4][5], it is likely that aberrant expression of MMPs in myeloid lineage cells plays critical roles in modulating CD11b+/Gr-1+ MDSCs homeostasis and cancer formation. Among MMPs, MMP12 is a 22-kDa secretory proteinase that is predominantly expressed in macrophages as previously reported[6]. MMP12 degrades extracellular matrix (ECM) components to facilitate tissue remodeling'. The expression of MMP12 in macrophages is induced in the lung of cigarette smokers[8]. Inactivation of the MMP12 gene in knock-out mice demonstrates a critical role of MMP12 in smoking-induced chronic obstructive pulmonary disease (COPD)[9], a disease highly related to lung cancer. From clinical studies, MMP12 correlates with early cancer-related deaths in non-small cell lung cancer (NSCLC), especially with those associated with tobacco cigarette smoke exposure[10,11]. Recently, it was demonstrated that MMP12 over-expression in alveolar type II epithelial cells directly triggered lung tumorigenesis as a result of pulmonary inflammation[11]. However, how MMP12 triggers inflammation is not understood.

Since MMP12 over-expression is highly associated with smoking-induced inflammatory cell infiltration in the lung, characterization of MMP12 over-production will facilitate understanding of the initiation and progression of lung cancer and COPD as related to smoking Interestingly enough, MMP12-overexpression was induced in bone marrow Lin⁻ and myeloid progenitor cells of the smoking-like lal−/− mouse model[20] (FIG. 8&8), in which LAL deficiency caused abnormal hematopoietic progenitor cell development and MDSC expansion[15]. As a downstream target gene of lysosomal acid lipase[20,21], MMP12 potentially regulates myelopoiesis. To mimic the clinical setting, a conditional myeloid-specific MMP12 over-expression mouse system was successfully created (FIGS. 8, 9, 10, 11). This animal model allows one to systematically characterize the pathogenic consequences of myeloid MMP12 up-regulation and reveal the mechanisms underneath.

Figure 8:
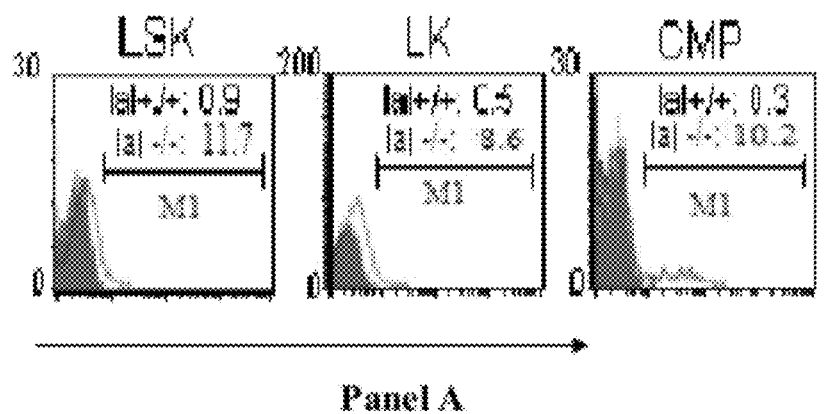
FIG. 8A.—Representative flow cytometry of MM12 expression in manrou progenitor cell, of wild type (lal+/+) and (lal−/−) mice.
Figure 8:
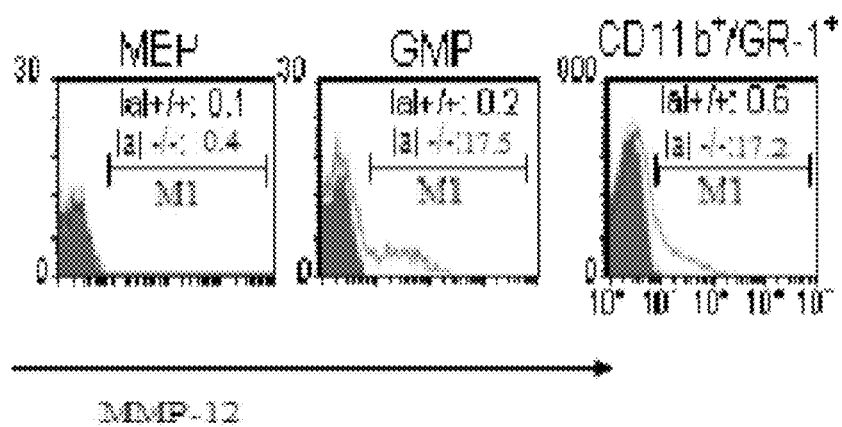
Figure 9A:
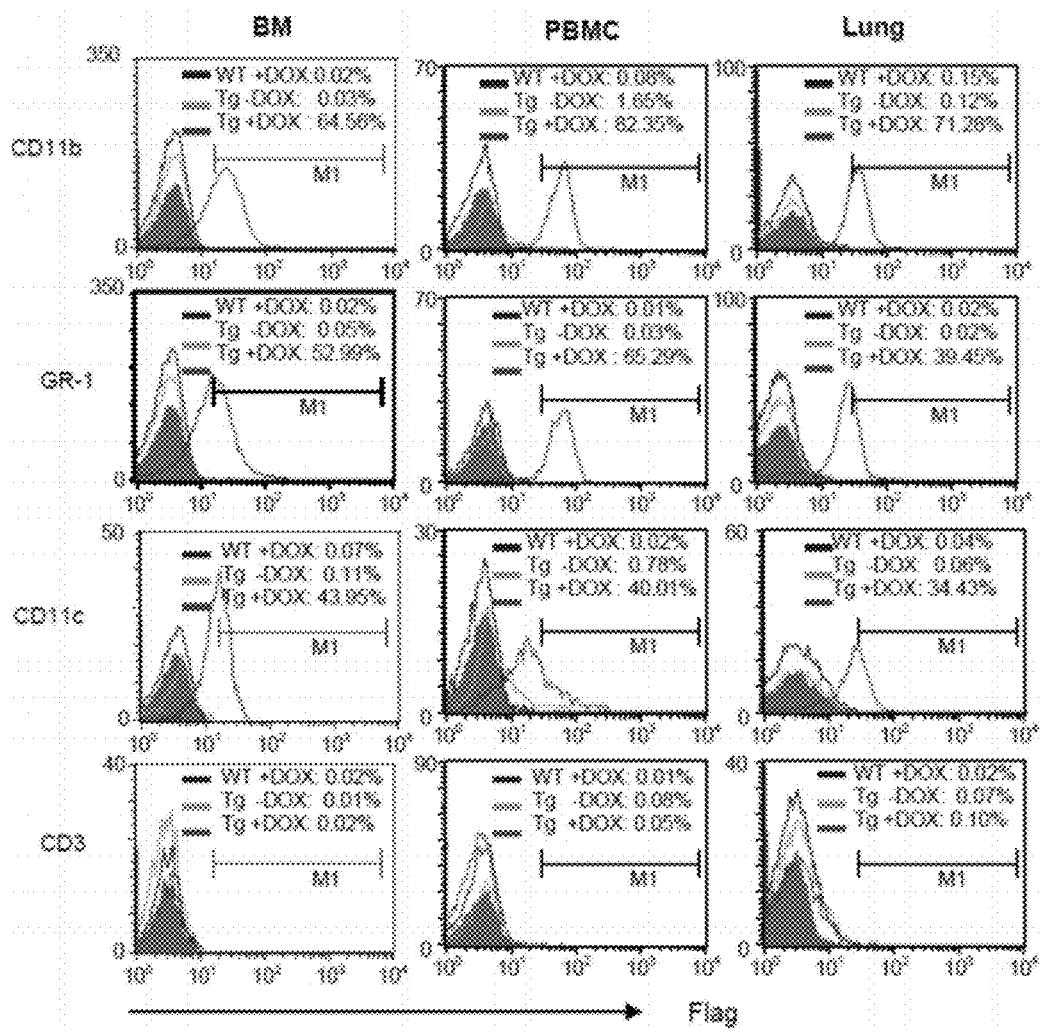
FIG. 9A.—Flow cytometry on bone marrow (BM), blood (PBMC) and lung of DOX treated or untreated (TG) c-fms-rtTA/(TcTO)$_7$-CMv-MMP12 bitransgenic mice.
Figure 9B:
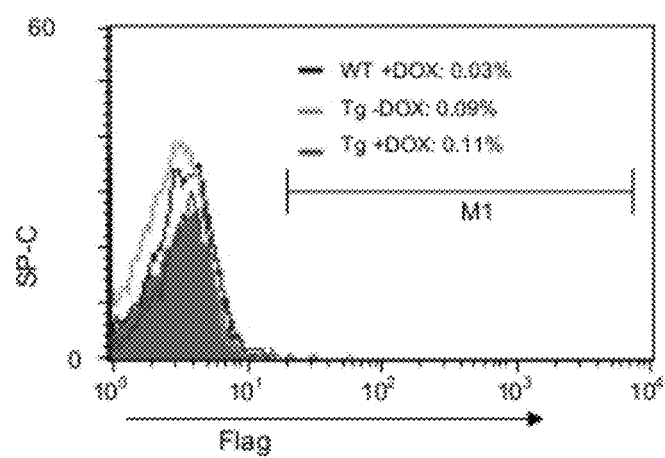
FIG. 9B.—Flow cytometry data related to FIG. 9A.
Figure 10:
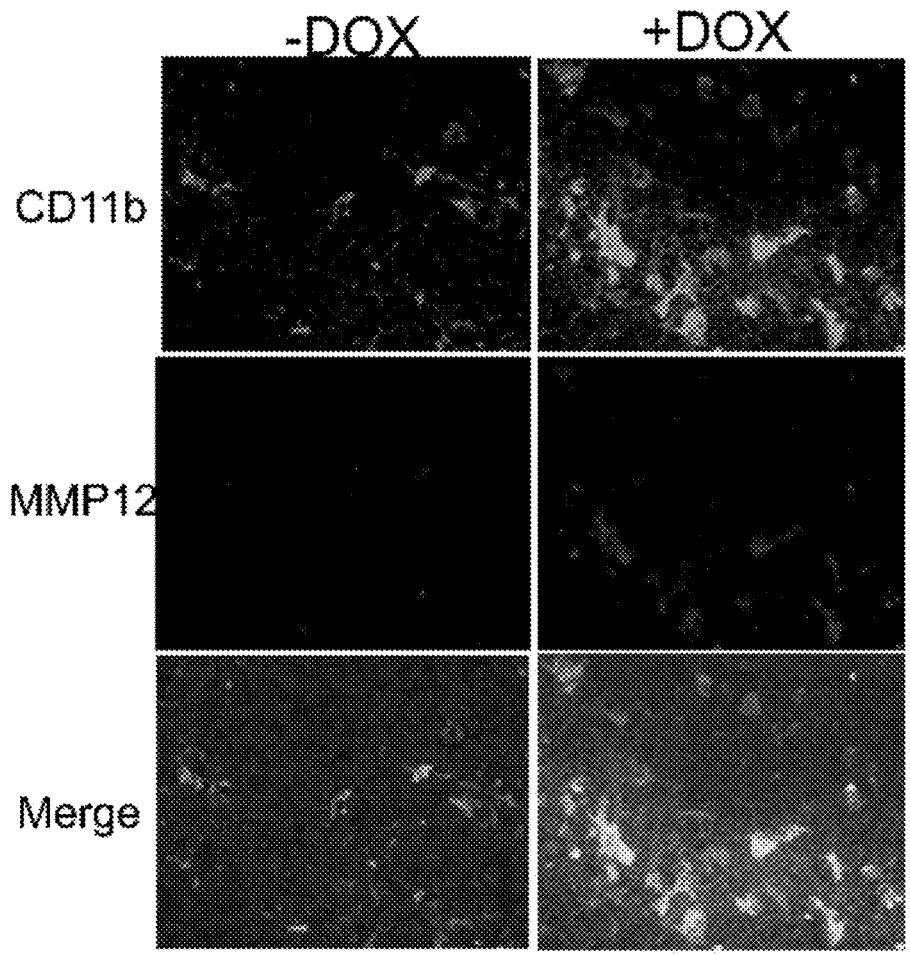
FIG. 10.—Photomicrographs of spleen tissue from bitransgenic mice treated or untreated with DOX and stained with anti-Flag Ab.

Referring now to FIGS. 8, 9, 10 and 11. Myeloid specificity of doxycycline-controlled c-fms-rtTA/(TetO)$_7$-CMV-MMP12 bitransgenic mice. Referring now to FIG. 8. Representative flow cytometry profiles of MMP12 expression in bone marrow progenitor cells of wild type (lal+/+) and lal−/− mice. In gated bone marrow progenitor cells, the numbers of MMP12⁺ cells were analyzed by flow cytometry. Isotype controls were shown as the shaded areas in each assay. The percentage numbers were calculated based on M1, a histogram marker excluding isotypic negative control. Referring now to FIG. 9. Cells from the bone marrow (BM), (PBMC) and lung of 3-month doxycycline-treated wild type mice (WT +DOX; blue line), doxycycline-treated (Tg +DOX; red line) or untreated (Tg −DOX; green line) c-fms-rtTA/(TetO)$_7$-CMV-MMP12 bitransgenic mice were stained with anti-Flag Ab in combination with cell surface markers. In gated CD11b⁺, CD11c⁺, GR-1⁺, CD3⁺ and SP-C (lung alveolar type II epithelial cell specific marker) cells, the numbers of the Flag⁺ cells were analyzed by flow cytometry. Isotype controls were shown as the shaded areas in each assay. The percentage numbers were calculated based on M1. Referring now to FIG. 10. Double Immunofluorescence staining of MMP12 (red) and CD11b (green) was performed in the spleen of 3-month doxycycline-treated (+DOX) or untreated (−DOX) bitransgenic mice. The spleens were washed with PBS and dehydrated by a series of increasing ethanol concentrations, followed by paraffin embedding. Tissue sections were cut to 5 μm thick and doubly stained with MMP12 rabbit antibody (Santa Cruz Biotech, Santa Cruz, Calif., USA) and CD11b mouse antibody (eBioscience). A Cy2-conjugated donkey anti-rabbit IgG and a Cy3-conjugated donkey anti-mouse IgG (Jackson ImmunoResearch, West Grove, Pa., USA) were used as the secondary antibodies. Blue staining (DAPI) represents cell nuclei. Referring now to FIG. 11A. MMP12 enzymatic activity was analyzed in the serum of doxycycline-treated wild type (WT) mice, doxycycline-treated (+DOX) and untreated (−DOX) bitransgenic (Tg) mice. n=4, **P<0.01. Referring now to FIG. 11B. Total mRNA was purified from blood CD11b⁺/GR-1⁺ cells of 3 month doxycycline-treated (+DOX) or untreated (−DOX) wild type (WT) mice or bitransgenic mice (Tg). Real-Time PCR was used to measure the level of MMP12 mRNA expression as normalized by glyceraldehyde-3-phosphate dehydrogenase (GAPDH) mRNA expression. n=4, P<0.01.

Generation of c-fms-rtTA/(TetO)$_7$-CMV-MMP12 Bitransgenic Mice

To test if MMP12 is up-regulated in bone marrow progenitor cells in a disease model, the smoking-like lal−/− mouse model[20] was utilized. Lysosomal acid lipase (LAL) hydrolyzes cholesteryl esters and triglycerides to generate free fatty acids and cholesterol in lysosomes of cells. Disruption of LAL expression leads to abnormal development of hematopoietic progenitor cells skewed toward the myeloid lineage cells[15]. Since MMP12 is a downstream gene of LAL[20,21], the MMP12 expression level was assessed in bone marrow progenitor cells of lal−/− mice. As demonstrated in FIG. 8, the MMP12 level was very low in the bone marrow progenitor cells of wild type mice, but was highly induced in LSK, LK, CMP, GMP and CD11b⁺Gr-1⁺ cells of lal−/− mice. Therefore, abnormal MMP12 over-expression was correlated with abnormal development of bone marrow progenitor cells in the smoking-like lal−/− disease model.

Figure 11A:
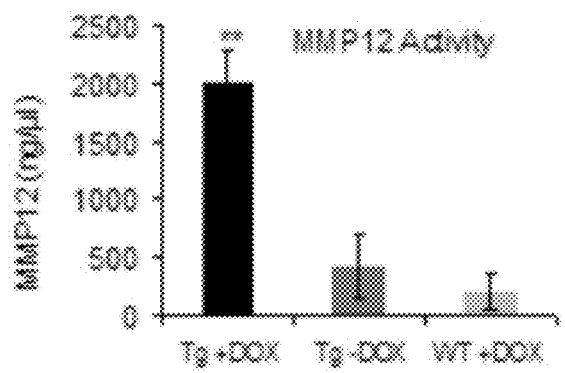
FIG. 11A. Graph of MMP12 enzyme activity measured in the serum of both WT and bitransgenic mice either treated or untreated with DOX.
Figure 11B:
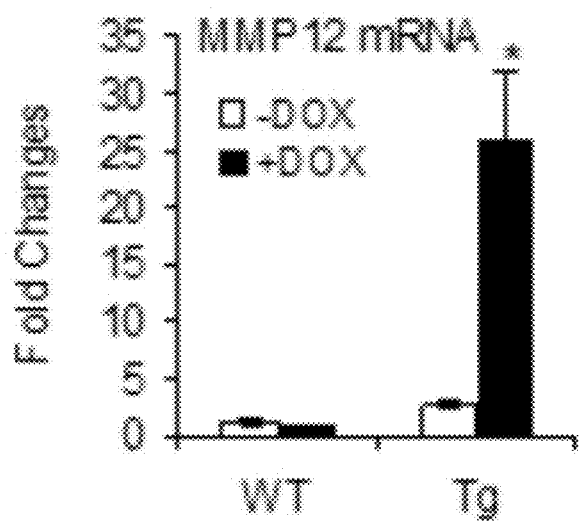
FIG. 11B. Graph of total mRNA recovered from the blood of CD11b+/GR-1+ cells from WT and bitransgenic mice treated or untreated with DOX.

To test if MMP12 causes abnormal development of bone marrow progenitor cells, a doxycycline-controlled bitransgenic mouse model was generated to specifically direct MMP12 over-expression in myeloid cells. In this system, a Flag sequence was added at the C terminus of the MMP12 cDNA to distinguish exogenous MMP12-Flag fusion protein from endogenous MMP12 protein. After bitransgenic mice were treated with or without doxycycline for 4 months, single-cell suspensions from the bone marrow, blood and lung were double stained with fluorochrome-conjugated Flag antibody and antibodies specific for macrophages, dendritic cells (DCs), neutrophils, or T cells. CD11b⁺ macrophages, Gr-1⁺ neutrophils and CD11c⁺ DCs all showed MMP12-Flag over-expression in all tested organs of doxycycline-treated mice compared with those of untreated mice (FIG. 8). As a negative control, there was no MMP12-Flag fusion protein expression in CD3⁺ T lymphocytes and SP-C⁺ lung epithelial cells regardless of doxycycline treatment. This result demonstrates that over-expression of MMP12-Flag fusion protein in c-fms-rtTA/(TetO)$_7$-CMV-MMP12 bitransgenic mice is myeloid lineage specific. Double immunofluorescence staining revealed increased infiltration of Gr-1+/CD11+ macrophages in the doxycycline-treated bitransgenic spleen (FIG. 10). The enzymatic activity assay showed an increased MMP12 activity in the plasma of $^{doxycycline}$-treated bitransgenic mice (FIG. 11A). Compared with the doxycycline-untreated plasma samples (430±270 ng/μL), the enzymatic product of MMP12 was 5-6 times higher in the doxycycline-treated plasma samples (2,020±260 ng/μL). Induction of MMP12 was at the gene expression level since mRNA expression in CD11b⁺/GR-1⁺ cells was much higher in doxycycline-treated samples than in untreated samples as monitored by the Real-Time PCR assay. Wild type mice showed no increase of MMP12 mRNA expression regardless of doxycycline treatment (FIG. 11B).

Referring now to FIG. 1. Systemic alteration of bone marrow progenitor and myeloid cells in c-fms-rtTA/(TetO)$_7$-CMV-MMP12 bitransgenic mice. FIG. 1A, Representative flow cytometry profiles of bone marrow progenitor populations, including CMPs, MEPs and GMPs from 3-month doxycycline-treated (+DOX) or untreated (−DOX) bitransgenic mice. The gating strategy was described in Materials and Methods; FIG. 1B, The percentages and total numbers of LSK, LK, CMP, MEP and GMP populations in the bone marrow of 3-month doxycycline-treated (+DOX) or untreated (−DOX) bitransgenic mice. Results are the mean±SD, n=4. *P<0.05. LK: IL7Rα⁻Lin⁻c-Kit⁺Sca-1⁻ progenitor; LSK: IL7Rα⁻Lin⁻Sca-1⁺c-Kit⁺ progenitor; CMP: Common myeloid progenitor; GMP: Granulocyte-monocyte progenitor; MEP: Megakaryocyte-erythroid progenitor; FIG. 1C, Granulocyte colony formation in 5×10⁴ bone marrow cells from doxycycline-treated (+DOX) or untreated (−DOX) bitransgenic mice in methylcellulose containing various concentrations of G-CSF. Colony counts were performed at day 10. Results are the mean of five independent studies, n=5; FIG. 1D, A representative flow cytometry analysis of CD11b$^+$ and GR-1$^+$ cells in the bone marrow and spleen of 3-month doxycycline-treated wild type (WT) mice, doxycycline-treated (+DOX) bitransgenic mice, doxycycline-untreated (−DOX) bitransgenic mice, and doxycycline-treated (for 2 months) followed by doxycycline-removal (for 1 month) bitransgenic mice, FIG. 1E, Absolute cell numbers of CD11b$^+$/GR-1$^+$ cells in the bone marrow and spleen based on analyses of the above experimental groups. Results are the mean±SD, n=5, *P<0.05.

Figure 1B:
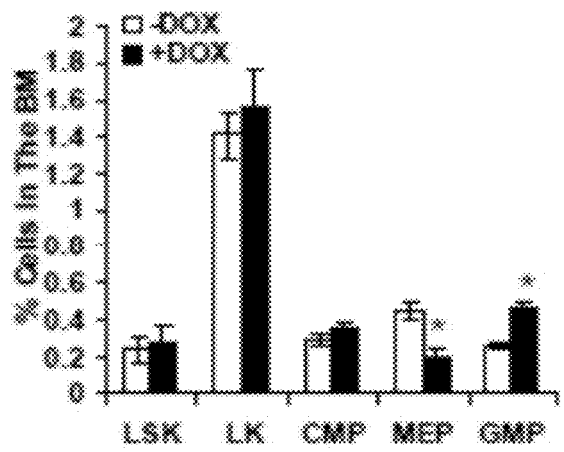
FIG. 1B.—Percentages of total numbers of LSK, LK, CMP, MEP and GMP populations in the marrow of bitransgenic mice treated or untreated with DOX.
Figure 1B:
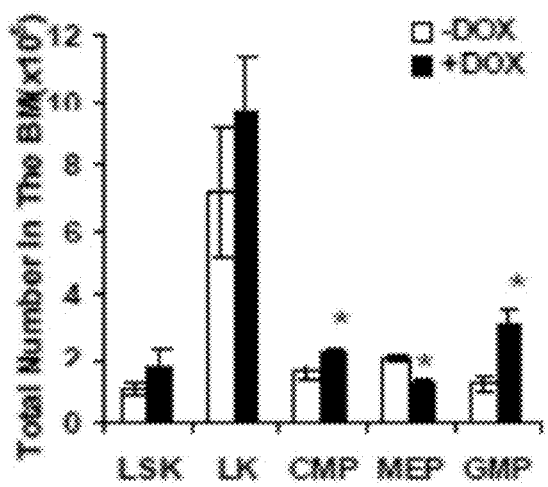
Figure 1C:
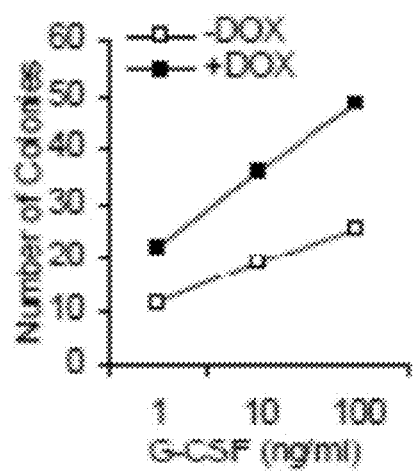
FIG. 1C.—Measure of granulocyte colony formulation from bitransgenic mice treated or untreated with DOX.

In order to assess the effect of myeloid MMP12 over-expression on the differentiation of hematopoietic progenitor cells in vivo, bone marrow cells were harvested from bitransgenic mice with or without 3-month doxycycline treatment. Over-expression of MMP12 significantly increased the frequencies and numbers of the CMP (IL7Rα_Lin$^-$Sca-1$^-$c-Kit$^+$ CD34$^+$FcRII/III$^{low}$) and GMP (IL7Rα$^-$Lin$^-$Sca-1$^-$ c-Kit$^+$ CD34$^+$ FcRII/III$^+$) progenitor populations, and decreased the frequency and number of the megakaryocyte/erythrocyte progenitor (MEP) population (IL7Rα$^-$Lin$^-$Sca-1$^-$c-Kit$^+$CD34$^-$ FcRII/III$^-$) in the bone marrow. The frequencies and numbers of the LK (IL7Rα$^-$Lin$^-$c-Kit$^+$Sca-1) and LSK (IL7Rα$^-$Lin$^-$ Sca-1$^+$c-Kit$^+$) populations[14] remained relatively unchanged (FIG. 1A-B). These results suggest that over-expression of MMP12 stimulates hematopoietic progenitor cells skewing toward the myeloid lineage cells. This has been confirmed by a hematopoietic colony forming assay, in which bone marrow cells from doxycycline-treated bitransgenic mice generated 2-3 fold more colonies by granulocyte colony-stimulating factor (G-CSF) stimulation than those from doxycycline-untreated mice in methylcellulose culturing in a dosage dependent manner (FIG. 1C).

Figure 1D:
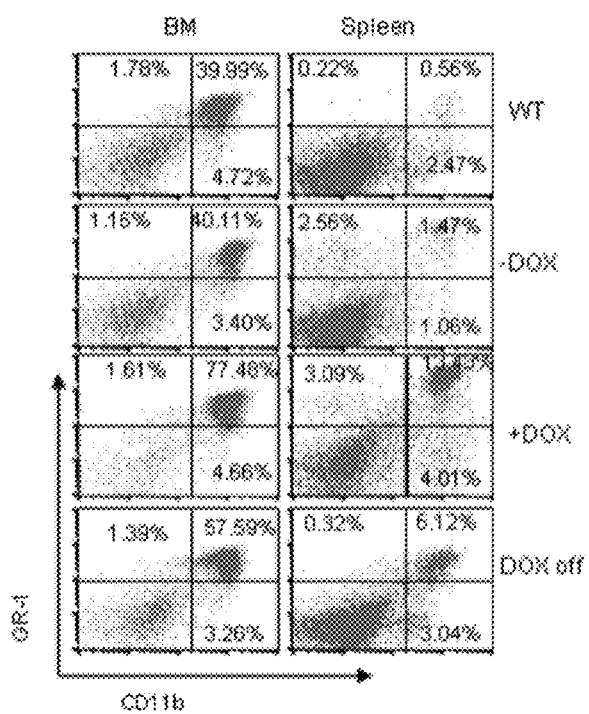
FIG. 1D.—Representative flow cytometry of CD11b and GR-1$^+$ cells in the marrow and spleens of WT bitransgenic mice either treated or untreated with DOX.
Figure 1E:
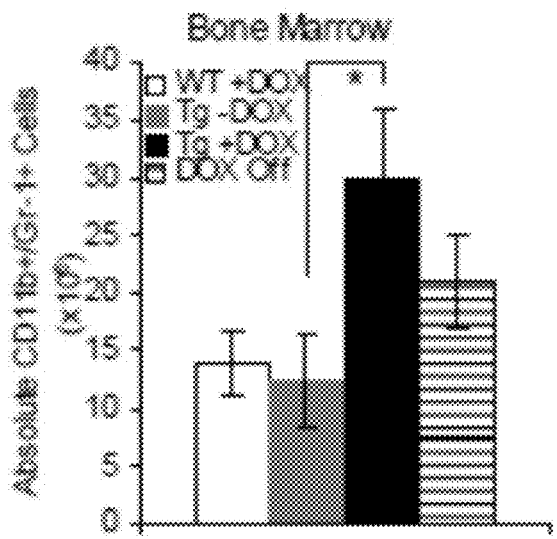
FIG. 1E.—Graphic showing absolute number of CD11b+/GR-1+ cells in the marrow and spleens of mice used in the experiments.
Figure 1E:
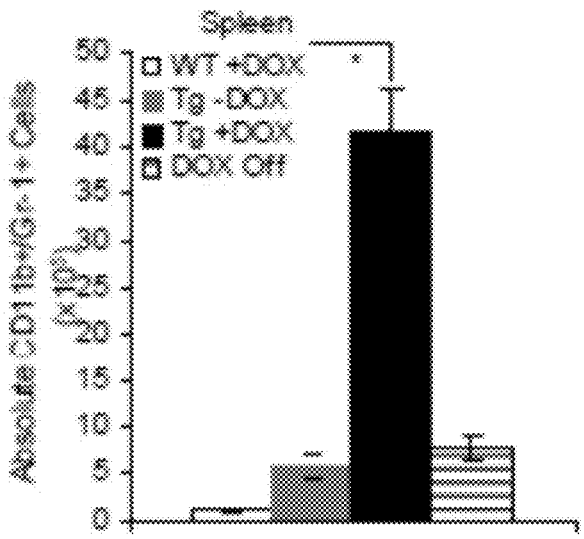

To further analyze how the hematopoietic progenitor defect in the bone marrow affects myelopoiesis, myeloid cells in bitransgenic mice were measured by flow cytometry with Gr-1 and CD11b antibody staining. Compared with wild type and doxycycline-untreated bitransgenic mice, both percentage and absolute numbers of the immature CD11b$^+$/GR-1$^+$ myeloid cell population were increased in the spleen of doxycycline-treated bitransgenic mice (FIGS. 1D-E). In a doxycycline on and off study (2-month doxycycline treatment followed by 1-month untreatment), both percentage and absolute numbers of CD11b$^+$/GR-1$^+$ cells were reduced, but still higher than those in untreated bitransgenic mice (FIG. 1E).

MMP12 Suppresses T Cell Proliferation and Function In Vivo

Referring now to FIG. 2, T cell decrease in c-fms-rtTA/(TetO)$_7$-CMV-MMP12 bitransgenic mice. FIG. 2A, Flow cytometry analysis of CD4$^+$ and CD8$^+$ cells from the spleen of 3-month doxycycline-treated wild type (WT) mice, doxycycline-treated (+DOX), doxycycline-untreated (−DOX) bitransgenic mice, and doxycycline-treated (for 2 months) followed by doxycycline-removal (for 1 month) bitransgenic mice (on/off). Results are the mean±SD, n=5, *P<0.05; FIG. 2B, A representative flow cytometry analysis showing the FoxP3 and CD25 profiles among total CD4$^+$ T cells from the spleen of 3-month doxycycline-treated wild type (WT) mice, doxycycline-treated (+DOX), untreated (−DOX) bitransgenic mice and doxycycline-treated (for 2 months) followed by doxycycline-removal (for 1 month) bitransgenic mice (on/off). FIG. 2C, Absolute cell numbers of FoxP3$^+$ Treg cells among total CD4$^+$ T cells were calculated based on analyses of the above experimental groups. Results are the mean±SD, n=5, *P<0.05; FIG. 2D, CFSE-labelled CD4$^+$ T cells were stimulated with anti-CD3 mAb plus anti-CD28 mAb for 4 days in the presence or absence of Treg cells isolated from the spleens of wild type (WT), doxycycline-treated (+DOX) or untreated (−DOX) bitransgenic mice. The ratio between Treg:CD4$^+$ T cells was 1:1. Proliferation of labelled CD4$^+$ T cells was analyzed by flow cytometry. Peaks represent cell division cycle; FIG. 2E, Wild type CD4$^+$ T cells from the spleen were cultured and stimulated with anti-CD3 mAb plus anti-CD28 mAb in the absence and presence of inactivated (inact) or activated (act) MMP12. After 72 hours, T cells were stained with anti-CD69 and CD4 antibodies. A representative flow cytometry analysis is demonstrated; FIG. 2F, The concentrations of secreted IL-2, IL-4 and IFNγ in the above cultured medium were measured by ELISA. Results are the mean±SD, n=5.

Figure 2A:
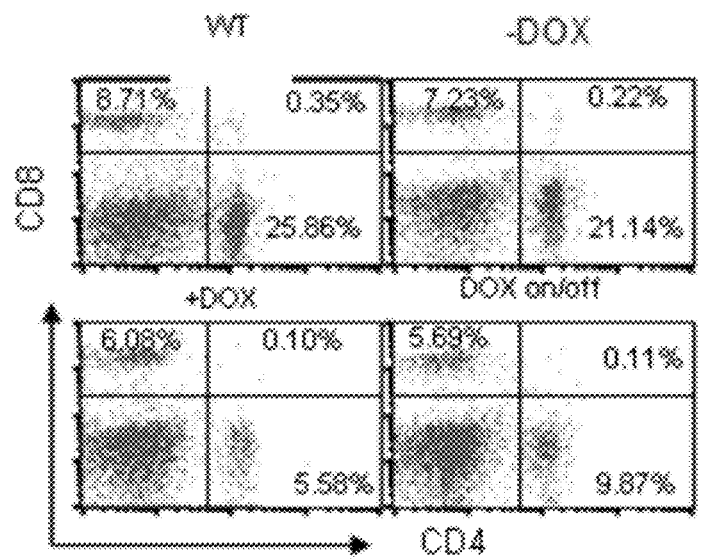
FIG. 2A. Reproductive flow cytometry showing CD4$^+$ and CD8$^+$ cells in spleen of WT and bitransgenic mice treated or untreated with DOX.
Figure 2B:
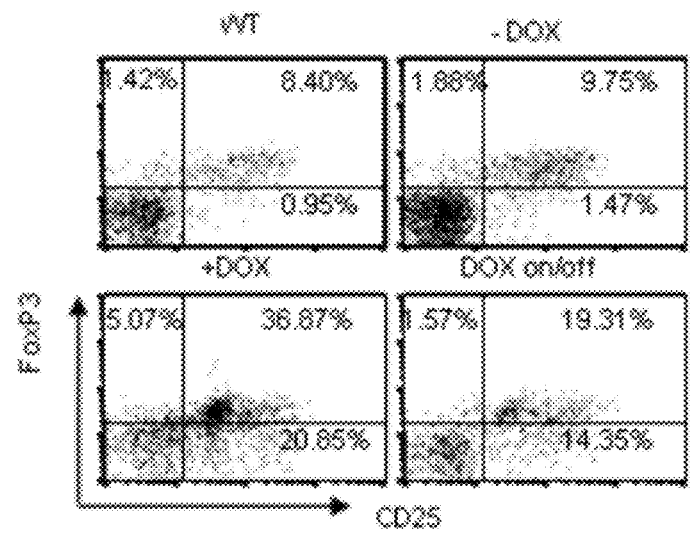
FIG. 2B.—Representative flow cytometry analyze showing FoxP3 and CD2T profiles of CD4+ T cells from the spleens of WT or bitransgenic mice treated or untreated with DOX.
Figure 2C:
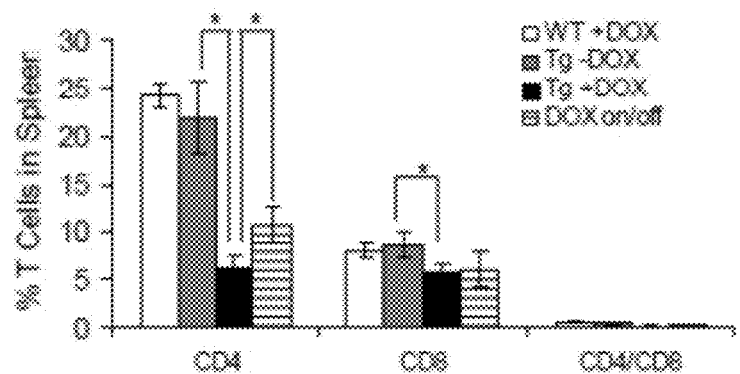
FIG. 2C.—Absolute number of Fox P3$^+$ Treg cells in total CB4$^+$ T cells found in experimental mice.
Figure 2C:
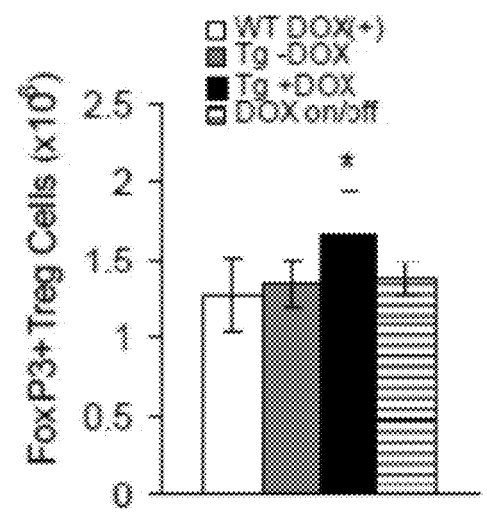
Figure 2D:
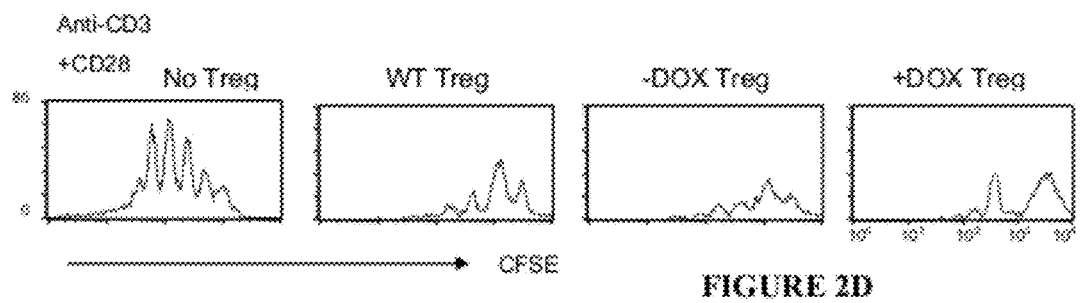
FIG. 2D.—Flow cytometry analysis of CFSE-labelled spleen CD4+ T cells stimulated with anti-CD3 mAb and anti-CD28 mAb in the presence and absence of Treg cells.
Figure 2E:
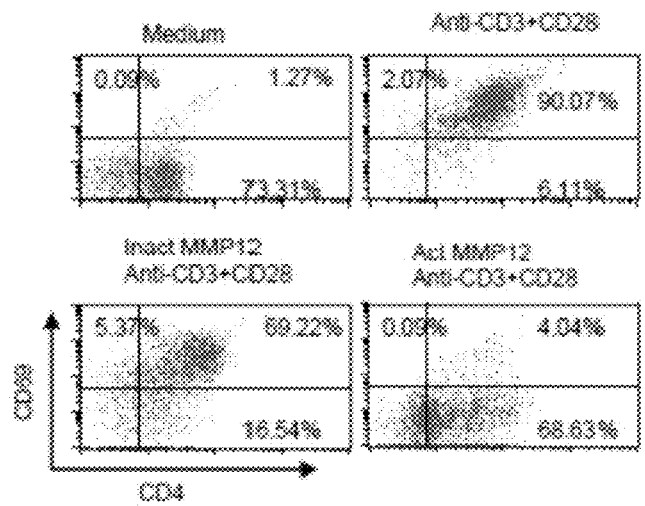
FIG. 2E. Flow cytometry analysis of wt CD4$^+$ T cells isolated for mouse spleens and stimulated with anti-CD3 mAb and anti-CD28 mAb in the presence of active or inactive MMP12.
Figure 2F:
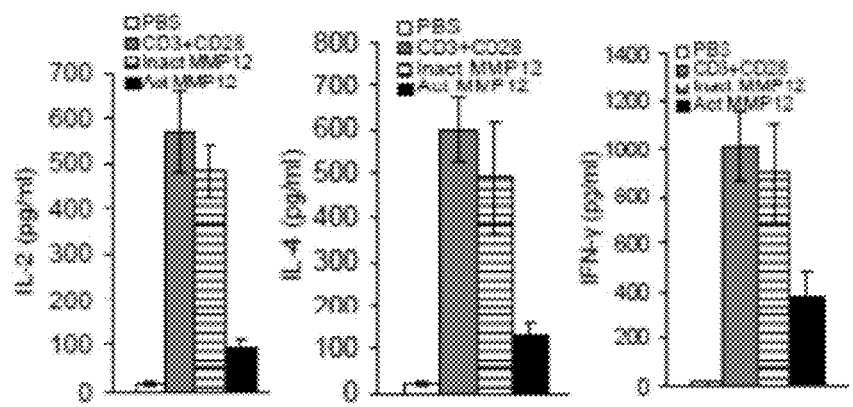
FIG. 2F.—Levels of IL-2, IC-4 and IFNγ found in cell culture media.

The CD4$^+$ T lymphocyte population was significantly decreased in the spleen of doxycycline-treated bitransgenic mice (5.58%) compared with that in untreated ones (21.14%), while the CD8$^+$ T lymphocyte population was less affected (FIG. 2A). In the doxycycline on and off study, decrease of the CD4$^+$ T lymphocyte population was only slightly recovered (9.87%), suggesting that this is an irreversible process. Among CD4$^+$ T cells, CD25$^+$/FoxP3 Treg cells were increased in both percentage (FIG. 2B) and absolute (FIG. 2C) numbers of doxycycline-treated mice. The Treg suppressive function on CD4+ T cells after anti-CD3 mAb plus anti-CD28 mAb stimulation remained relatively unaffected regardless of doxycycline treatment (FIG. 2D). To assess if MMP12 directly affects T cells, in vitro experiment was performed. When T cells were isolated from the wild type spleen and cultured in vitro, addition of activated-MMP12 dramatically inhibited the CD69 expression (an indicator of T cell activation) in cultured CD4$^+$ T cells after anti-CD3 mAb plus anti-CD28 mAb stimulation, from 90.07% in untreated T cells to 4.04% in the activated-MMP12-treated T cells (FIG. 2E). The culture medium showed decreased secretion of IL-2, IL-4 and IFNγ in the activated-MMP12 treated samples (FIG. 2F). However, expression of Treg marker FoxP3 was not altered (data not shown). These in vitro results indicate that MMP12 exerts a direct inhibitory effect on CD4$^+$ T cell proliferation and function, but is not involved in production of Treg cells.

CD11b$^+$/Gr-1$^+$ MDSCs Inhibit T Cell Proliferation and Function

Referring now to FIG. 3. MDSCs suppression on CD4$^+$ T cells in c-fms-rtTA/(TetO)$_7$-CMV-MMP12 bitransgenic mice. FIG. 3A, CFSE-labelled CD4$^+$ T cells from the spleen of wild type (WT), doxycycline-treated (+DOX) and untreated (−DOX) mice were stimulated with anti-CD3 mAb plus anti-CD28 mAb for 3 days. Proliferation of labelled CD4$^+$ T cells was analyzed by flow cytometry. Peaks represent cell division cycles; FIG. 3B, Above cultured T cells were stained with anti-CD69 and CD4 antibodies and analyzed by flow cytometry. Results are the mean±SD, n=5, *p<0.05; FIG. 3C, CFSE-labelled wild type splenic CD4$^+$ T cells were stimulated with anti-CD3 mAb plus anti-CD28 mAb for 4 days in the presence or absence of CD11b$^+$/Gr-1$^+$ cells from the spleen of wild type (WT), doxycycline-treated (+DOX) or untreated (−DOX) bitransgenic mice. The ratio between CD11b$^+$/Gr-1$^+$ cells:CD4$^+$ T cells was 1:5. Proliferation of labelled CD4$^+$ T cells was analyzed by flow cytometry. Peaks represent cell division cycles. PBS was negative stimulation control; FIG. 3D, The concentrations of secreted IL-2 and IL-4 in the above cultured medium were measured by ELISA. Results are the mean±SD, n=5; FIG. 3E, CFSE-labelled CD4$^+$ T cells were co-cultured with CD11b$^+$/Gr-1$^+$ cells as described in (C). After 72 hours, co-cultured cells were stained with anti-CD69 and CD4 antibodies for flow cytometry analysis. PBS was negative stimulation control; FIG. 3F, Wild type CD4$^+$ T cells were co-cultured with CD11b$^+$/Gr-1$^+$ cells as described in FIG. 3C, and labelled with Annexin V and CD4 antibodies for the analysis by flow cytometry. Results are the mean±SD, n=5.

Figure 3A:
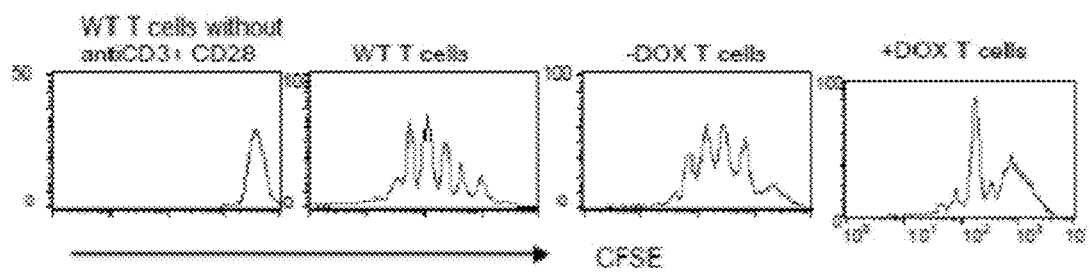
FIG. 3A.—Flow cytometry analysis of CFSE-labelled CD4$^+$ T spleen cells from WT and bitransgenic mice treated or untreated with DOX.
Figure 3B:
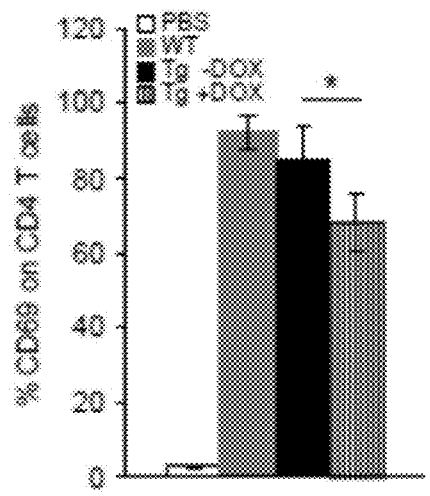
FIG. 3B.—Graph of T-cells, from mice spleens stained with anti-CA69 and CD4 antibodies.
Figure 3C:
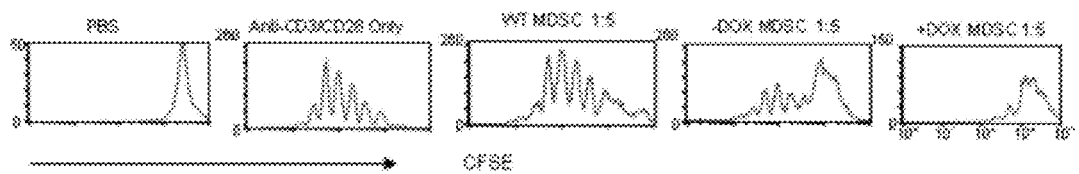
FIG. 3C.—Proliferation of CFSE-labelled CD4$^+$ T cells analyzed by flow cytometry. Cells were stimulated with anti-CD3 mAb and anti-CD28 mAb. The cells are from the spleens of WT or bitransgenic mice treated with or without DOX in the process or absence of CD116$^+$/Gr-1$^+$ cells.
Figure 3D:
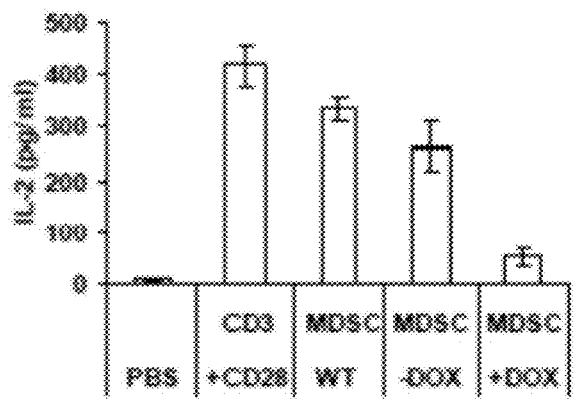
FIG. 3D.—Levels of IL-2 and IL-4 in mouse spleen cell cultures measured by ELISA.
Figure 3D:
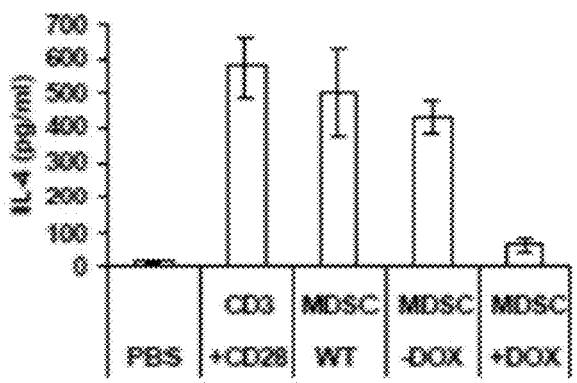
Figure 3E:
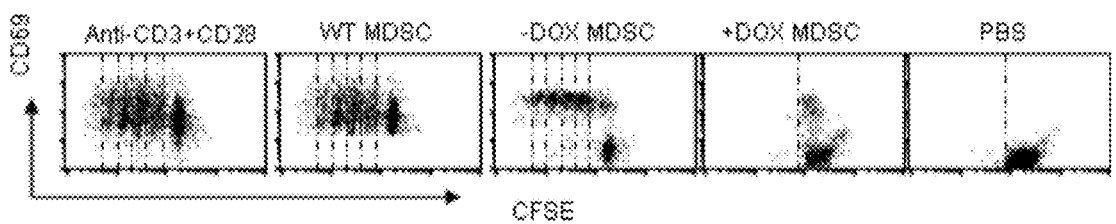
FIG. 3E.—Flow cytometry analysis of CFSE labelled CD4$^+$ T cells co-cultured with CD116$^+$ 16r-1+ (see FIG. 3. C).
Figure 3F:
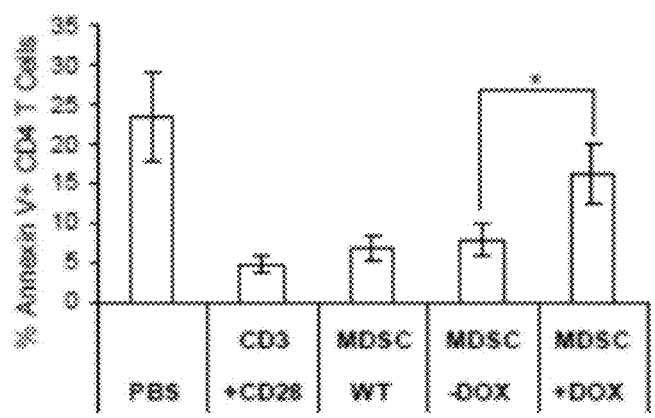
FIG. 3F.—Flow cytometry analysis of WT CD4$^+$ T cells co-cultured with CD116$^+$/Gr-1$^+$ cells (see FIG. 3C) and labelled with Annexin V and CD4 antibodies.

Decrease of the CD4+ T cell population in doxycycline-treated bitransgenic mice was due to decreased cell proliferation as assessed by the CFSE-labeling (FIG. 3A) and CD69 expression studies (FIG. 3B). In addition to the MMP12 direct inhibitory effect, MDSCs expansion may also contribute to T cell decrease in bitransgenic mice. To test this assumption, CFSE-labelled wild type CD4+ T cells were cultured in vitro and stimulated with anti-CD3 mAb plus anti-CD28 mAb for 3 days in the presence or absence of CD11b+/Gr-1+ cells (MDSC: T ratio=1:5) from wild type mice (WT MDSCs), DOXcycline-treated (+DOX MDSCs), or untreated (−DOX MDSCs) bitransgenic mice. CD11b+/Gr-1+ cells from DOXcycline-treated bitransgenic mice showed the strongest inhibition on proliferation of wild type CD4+ T cells (FIG. 3C). This inhibition was further confirmed by a significant reduction of IL-2 and IL-4 secretion, implicating a functional impairment of CD4+ T cells by CD11b+/Gr-1+ cells from DOXcycline-treated bitransgenic mice (FIG. 3D). Unlike the observation made in the MMP12 treatment study (FIG. 2F), CD4+ T cells co-cultured with CD11b+/Gr-1+ cells from DOXcycline-treated bitransgenic mice retained the ability to secrete IFN-γ (data not shown). Furthermore, CD69 expression in CD4+ T cells was dramatically inhibited by CD11b+/Gr-1+ cells from DOXcycline-treated bitransgenic mice in the CFSE-labeling FACS study (FIG. 3E). To determine whether CD4+ T cell reduction is associated with apoptosis, Annexin V analysis was performed, in which CD4+ T cells were co-stained with fluorochrome-conjugated Annexin V antibody and anti-CD4 antibody. Again, CD4+ T cells showed the highest apoptotic activity when co-cultured with CD11b+/Gr-1+ cells from doxycycline-treated bitransgenic mice (FIG. 3F). There was no distinctive apoptotic activity of CD4+ T cells between co-culture of wild type CD11b+/Gr-1+ cells or CD11b+/Gr-1+ cells from DOXcycline-untreated bitransgenic mice. These observations indicate that aberrant CD11b+/Gr-1+ cells caused by myeloid over-expression of MMP12 were able to inhibit T cell proliferation and function.

MMP12 Up-Regulates Pro-Inflammatory Cytokines and Activates Intracellular Signaling Molecules in CD11b+/Gr-1+ MDSCs In Vivo and In Vitro Referring now to FIG. 4. Up-regulation of cytokines and activation of oncogenic intracellular signaling molecules in myeloid cells of c-fms-rtTA/(TetO)$_7$-CMV-MMP12 bitransgenic mice. FIG. 4A, Plasma samples were collected from 3-month doxycycline-treated wild type (WT) mice, doxycycline-treated (+DOX) or untreated (−DOX) bitransgenic mice. The concentrations of IL-1β, IL-6, MIP-2 and TNF-α were measured by ELISA. Results are the mean±SD, n=4; FIG. 4B, Intracellular staining of phosphor-Stat3 in bone marrow CMP and GMP progenitor cells of 3-month wild type (WT, blue line), doxycycline-treated (+DOX, red line) or untreated (−DOX, green line) bitransgenic mice by flow cytometry analysis. The shaded areas were isotype controls; FIG. 4C, Intracellular staining of phosphor-Stat3 in CD11b+/Gr-1+ cells from the blood, spleen and lung of 3-month doxycycline-treated (+DOX, red line) or untreated (−DOX, green line) bitransgenic mice by flow cytometry analysis. The shaded areas were isotype controls; FIG. 4.D, Lin− progenitor cells were isolated from the bone marrow of wild type mice and cultured in vitro in the absence and presence of inactivated (inact) or activated (act) MMP12. After 12 hours, cultured cells were stained with CD11b and Gr-1 antibodies for flow cytometry analysis; FIG. 4E, The concentrations of secreted IL-6 and IL-10 in the above cultured medium were measured by ELISA. Results are the mean±SD, n=4; FIG. 4F, In the above study, intracellular staining of phospho-Stat3, NFκBp65 and CEBP/α in CD11b+/Gr-1+ cells was analyzed by flow cytometry. The shaded areas were isotype controls; FIG. 4G, Lin− progenitor cells were isolated from the bone marrow of wild type and bitransgenic mice, and cultured in vitro. Cells were treated with doxycycline for 4 days followed by flow cytometry analysis with CD11b and Gr-1 antibody staining; FIG. 4.H, The concentrations of secreted IL-6 and IL-10 in the above cultured medium were measured by ELISA. Results are the mean±SD, n=4; FIG. 4I, In the above study, intracellular staining of phospho-Stat3 in CD11b+/Gr-1+ cells was analyzed by flow cytometry. The shaded area was isotype control; FIG. 4J, Wild type CD4+ T cells from the spleen were cultured and stimulated with anti-CD3 mAb plus anti-CD 28 mAb with or without doxycycline treatment. After 72 hours, T cells were stained with anti-CD69 and CD4 antibodies. A representative flow cytometry analysis is demonstrated.

Figure 4A:
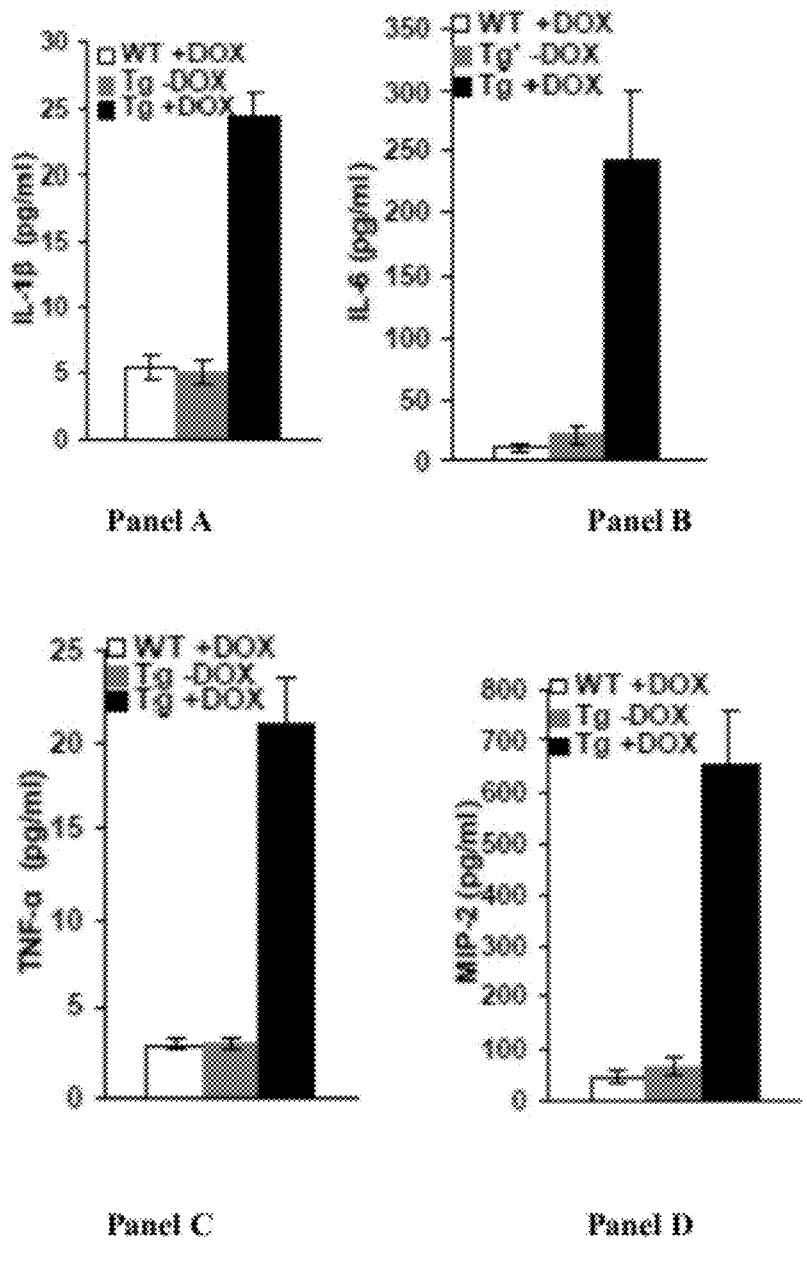
FIG. 4A. IL-1B, IL-6, MIP2 and TNFα measured by ELISA of the plasmas of WT or bitransgenic mice treated or untreated with DOX.

In order to elucidate the mechanisms by which MMP12 stimulates MDSCs expansion, several MDSCs-promoting cytokines were measured in the serum of bitransgenic mice by ELISA. Compared with doxycycline-untreated bitransgenic mice, the expression levels of IL-1β, IL-6, MIP-2 and TNF-α were abnormally increased in the plasma of doxycycline-treated bitransgenic mice (FIG. 4A). In addition, activation of Stat1, Stat3, Erk1/2, p38 and NFκB p65 intracellular signaling molecules was increased in CD11b+/Gr-1+ cells from the bone marrow, blood, spleen and lung of doxycycline-treated mice (Table 1).

TABLE 1

Expression of intracellular signaling molecules in CD11b+/Gr-1+ cells from 3-month doxycyline-treated c-fms/MMP12 mice

| | Bone Marrow | | PBMC | | Spleen | | Lung | |
|---|---|---|---|---|---|---|---|---|
| | −DOX | +DOX | −DOX | +DOX | −DOX | +DOX | −DOX | +DOX |
| pStat3 | 2.65 ± 1.21 | 11.00 ± 2.58 | 2.28 ± 0.45 | 45.37 ± 6.06 | 1.98 ± 0.18 | 15.29 ± 4.10 | 2.58 ± 1.35 | 12.99 ± 1.29 |
| pP38 | 1.68 ± 0.56 | 14.11 ± 2.32 | 1.75 ± 0.76 | 14.88 ± 4.28 | 1.55 ± 0.20 | 12.21 ± 3.09 | 2.05 ± 0.48 | 9.77 ± 1.23 |
| pErk | 3.71 ± 0.55 | 14.51 ± 3.12 | 2.36 ± 1.83 | 10.64 ± 0.99 | 2.88 ± 0.78 | 7.92 ± 1.34 | 3.97 ± 0.46 | 8.34 ± 0.57 |
| pNFκB | 2.45 ± 0.85 | 5.12 ± 1.64 | 2.05 ± 0.29 | 32.16 ± 8.58 | 1.63 ± 0.47 | 9.36 ± 2.00 | 1.76 ± 0.57 | 7.18 ± 1.68 |

Cells from the bone marrow, blood, spleen and lung of doxycyline-treated or untreated bitransgenic mice were stained with CD11b and GR-1 antibodies and followed by the intracellular staining with pStat3, pErk, pP38 or pNFkB antibody. Percentage numbers of different cells represent intracellular-stained positive cells in CD11b+/Gr-1+ cells from four independent experiments (n=4).

Figure 4B:
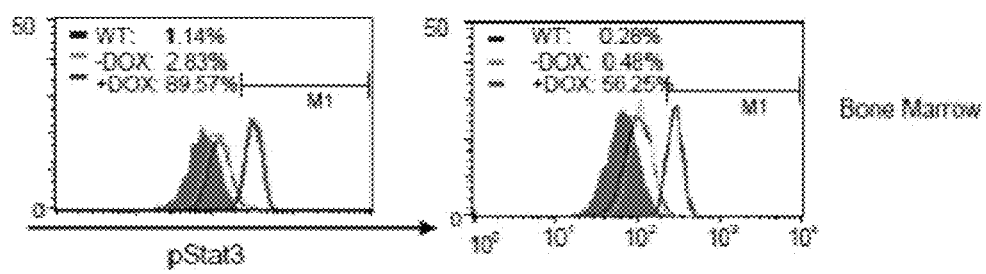
FIG. 4B.—Results from intercellular phospho-stat-3 staining CMP and GMP progonitor cells from WT or bitransgenic mice treated with or without DOX.
Figure 4C:
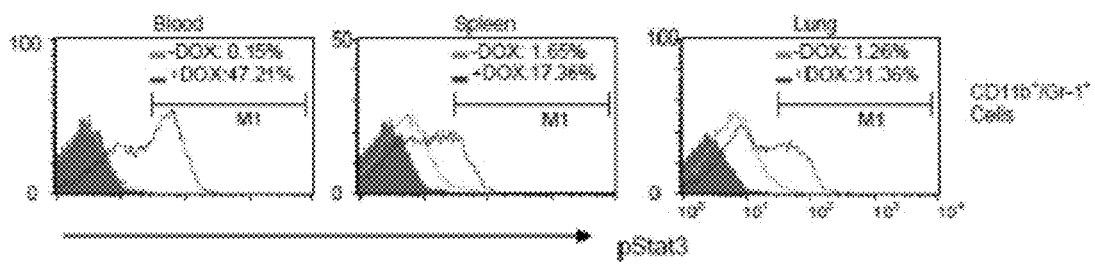
FIG. 4C.—Intercellular staining of phospho-stat-3 in CD116$^+$/Gr-1$^+$ cells from spleen, blood and lung of bitransgenic mice treated or untreated with DOX.
Figure 4D:
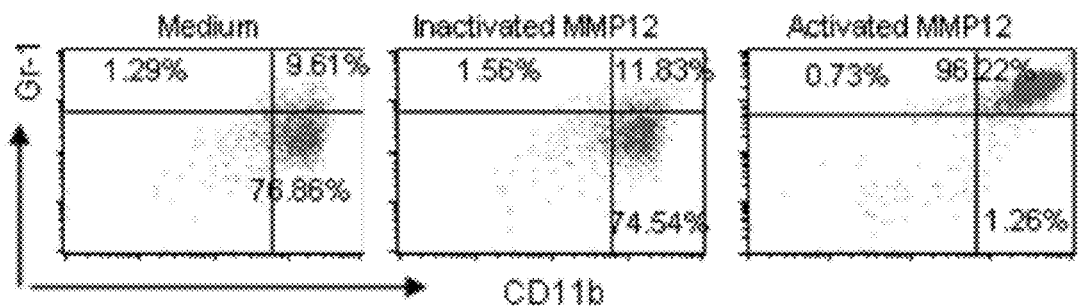
FIG. 4D.—Flow cytometry or Lin-1 progenitor cells from the bone marrow of WT mice culture in vitro in the presence or absence of active or inactive MMP12.
Figure 4E:
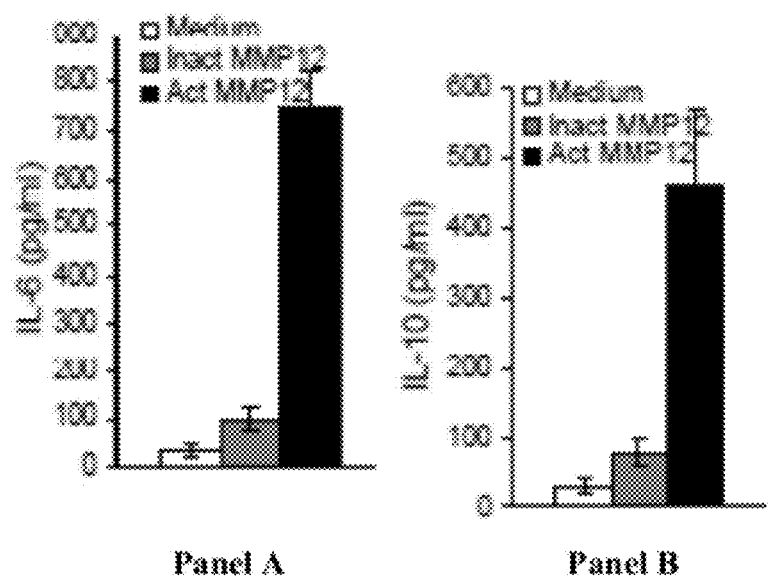
FIG. 4E.—Graphs of levels of IL-6, and IL-10 in the culture media determined by ELISA.
Figure 4F:
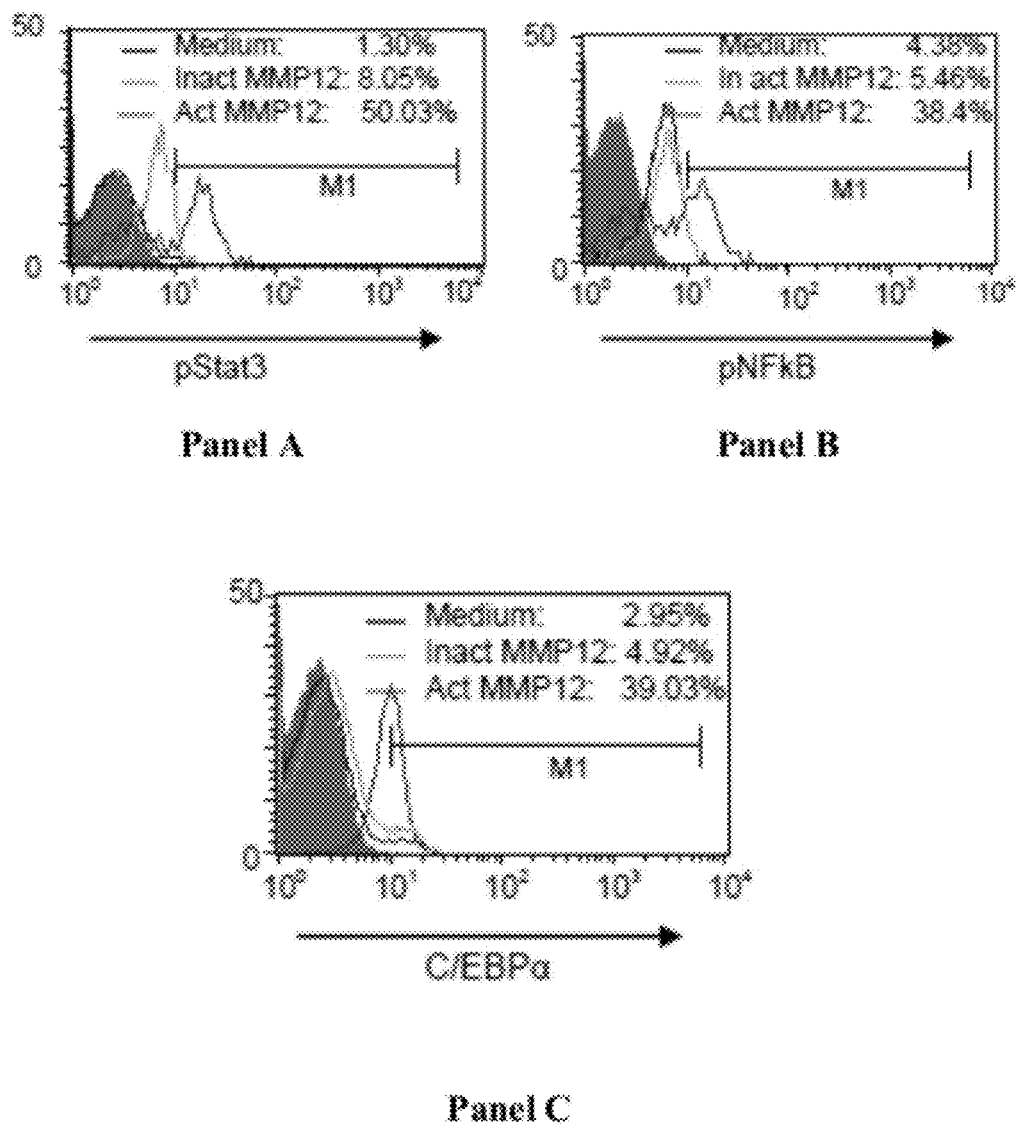
FIG. 4F.—Intercellular staining of phospho-stat-3 NFkBp65 and CEB/P2 in CD116+/Gr−/+ cells (shaded across are isotype controls).
Figure 4G:
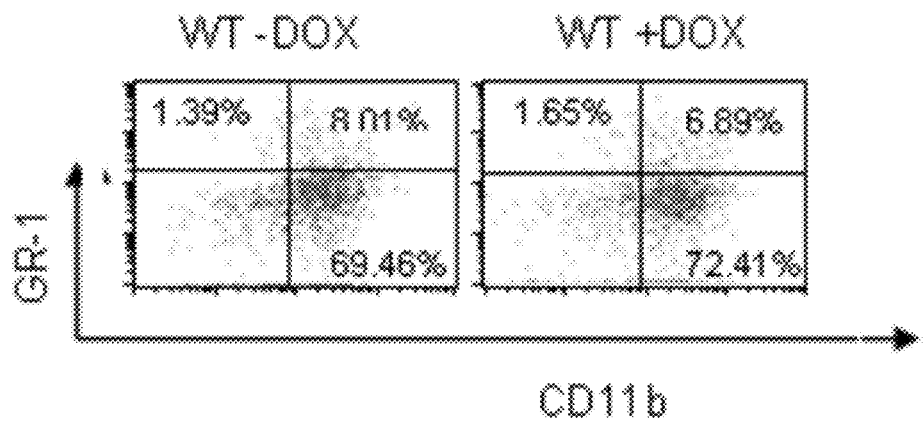
FIG. 4G. Floor cytometry analysis of LIN-1 progenitor cells isolated from the marrow of WT or bitransgenic mouse cells cultured in vitro.
Figure 4G:
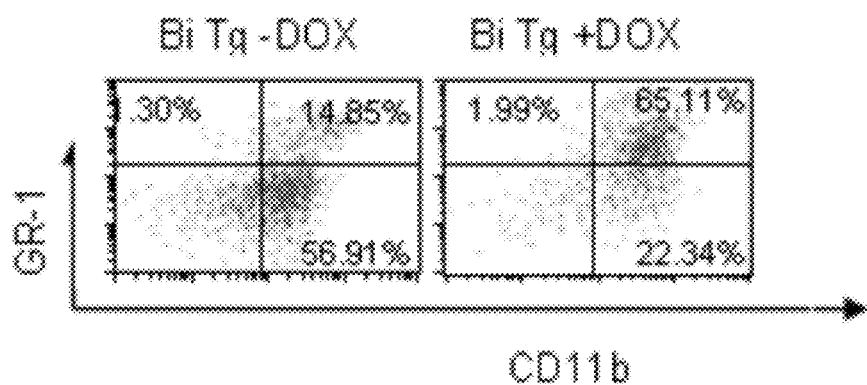
Figure 4H:
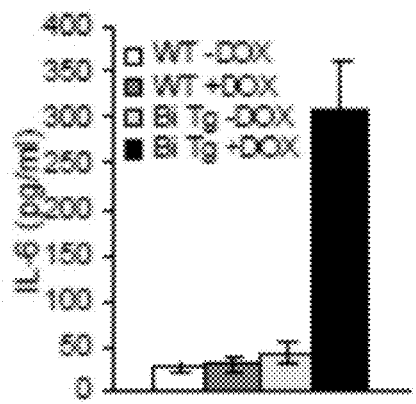
FIG. 4H.—Level of IL-6 and IL-10 in culture media (see FIG. 4G) measured by ELISA.
Figure 4H:
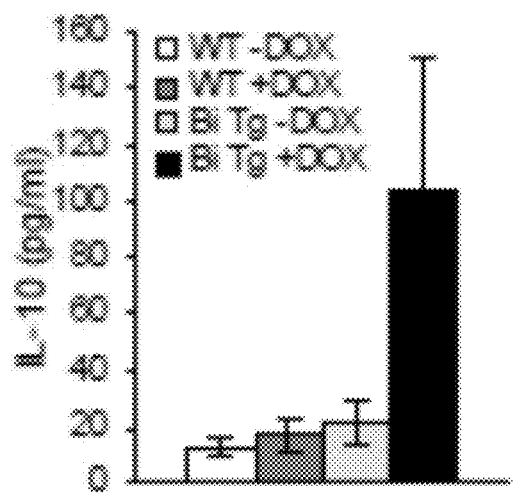
Figure 4I:
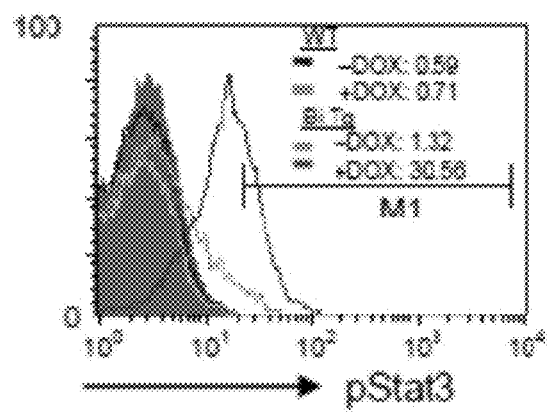
FIG. 4I.—Flow cytometry data of intercellular staining of phospho-stat-3 in CD116+/Gr-1+ cells.
Figure 4J:
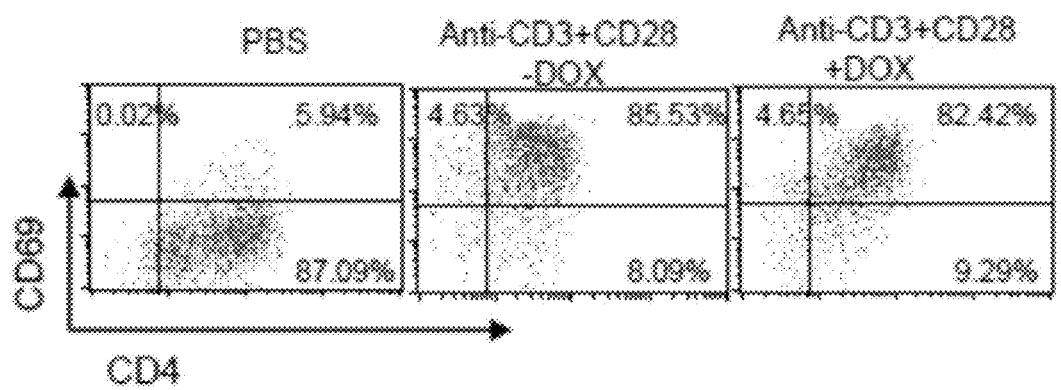
FIG. 4J.—Flow cytometry of WT CD4+ T cells from spleen cultures and stimulated with anti-CD3 mAb and anti-CD28 mAb treated or untreated with DOX cells stained with anti-CD69 and CD4 antibodies.

FIGS. 4B and 4C show an example of Stat3 analysis, in which Stat3 activation started at the myeloid lineage CMP and GMP stages from the bone marrow and in immature CD11b+/Gr-1+ Cells from the blood, spleen and lung of doxycyline-treated bitransgenic mice. In contrast, phospho-Stat2, Stat4, Stat5 and Stat6 showed no change between doxycyline-treated or untreated bitransgenic mice (data not shown). To assess if MMP12 directly alters myelopoiesis, an in vitro experiment was performed. When Lin⁻ progenitor cells were isolated from the bone marrow of wild type mice and cultured in vitro, addition of activated-MMP12 treated CD11b⁺/Gr-1⁺ cell expansion to 96.22% compared with 9.61% in the un-untreated Lin⁻ population (FIG. 4D). The culture medium showed increased concentrations of IL-6 and IL-10 in the activated-MMP12-treated samples (FIG. 4E). Activation of pStat3, pNFκB and C/EBPα (a transcription factor critical for myeloid cell differentiation) was significantly up-regulated in Lin⁻ cell-differentiated CD11b⁺/Gr-1⁺ cells (FIG. 4F). These surprising in vitro results indicate that MMP12 has a direct and profound influence on differentiation and commitment of hematopoietic progenitor cells skewing towards myeloid lineage cells. To confirm that MMP12 expression in Lin⁻ cells from bitransgenic mice indeed possesses the ability to stimulate differentiation of Lin⁻ cells to CD11b⁺/Gr-1⁺ cells, Lin⁻ cells were isolated from the bone marrow of wild type and bitransgenic mice, and cultured in vitro. Doxycyline treatment of cultured Lin⁻ cells from bitransgenic mice induced CD11b⁺/Gr-1⁺ cell expansion to 65.11% compared with 14.85% in the untreated cells (FIG. 4G). The culture medium showed increased concentrations of IL-6 and IL-10 in the doxycyline-treated samples (FIG. 4H). Activation of pStat3 was significantly up-regulated in Lin⁻ cell-differentiated CD11b⁺/Gr-1⁺ cells from doxycyline-treated samples (FIG. 4I). On the other hand, no changes were observed in Lin⁻ progenitor cells from wild type mice regardless of doxycyline treatment due to lack of MMP12 induction. Also, T cells showed no change in bitransgenic mice with doxycyline treatment (FIG. 4J).

Over-Expression of MMP12 Favors Oncogenic Microenvironment Change in the Lung

Referring now to FIG. 5. Over-expression of MMP12 activated the IL-6/Stat3 pathway in alveolar type II epithelial cells of c-fms-rtTA/(TetO)₇-CMV-MMP12 bitransgenic mice. FIG. 5A MMP12-specific enzymatic activity was analyzed in BALF from 3-month doxycyline-treated wild type (WT) mice, doxycyline-treated (+DOX) or untreated (−DOX) bitransgenic mice. Results are the mean±SD, n=5, . . . , p<0.01; FIG. 5B. The concentration of IL-6 was measured in BALF at 1, 3, 6, 9 months of doxycyline treatment (1 mo, 3 mo, 6 mo, 9 mo) by ELISA. Results are the mean±SD, n>4; FIG. 5C The purified lung alveolar type II epithelial cells were stained with SP-C (specific marker for alveolar type II epithelial cells) and phospho-Stat3. Phospho-Stat3 positive cells were analyzed by flow cytometry in gated SP-C-positive cells. The shaded area shows isotype controls; FIG. 5D. Real-time PCR analysis of Stat3 mRNA expression in the whole lung, alveolar macrophages, and alveolar type II epithelial cells from 3-month wild type (WT), doxycyline-treated (+DOX) or untreated (−DOX) bitransgenic mice. Results are the mean±SD, n>4; FIG. 5E. Real-time PCR analysis of Stat3 downstream cytokine and chemokine mRNA expression was assessed in the whole lung, alveolar macrophages, and alveolar type II epithelial cells in the same groups of mice as outlined in (D). Results are the mean±SD, n>4.

Figure 5A:
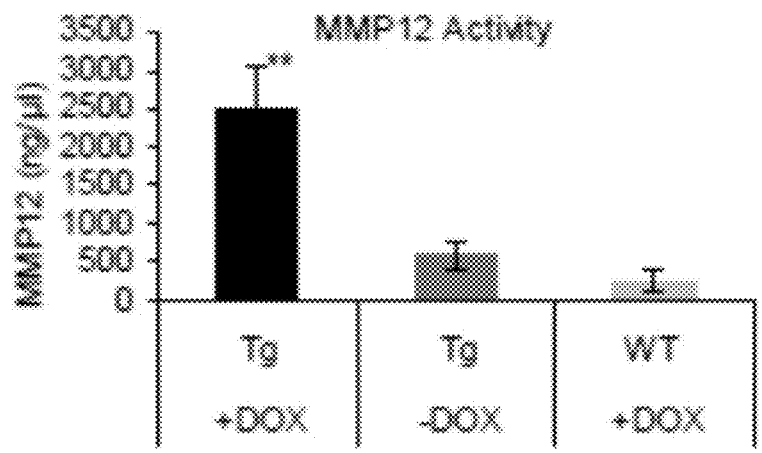
FIG. 5A.—Graph showing MMP12 activity in BALF from WT and bitransgenic mice either treated or untreated with DOX.
Figure 5B:
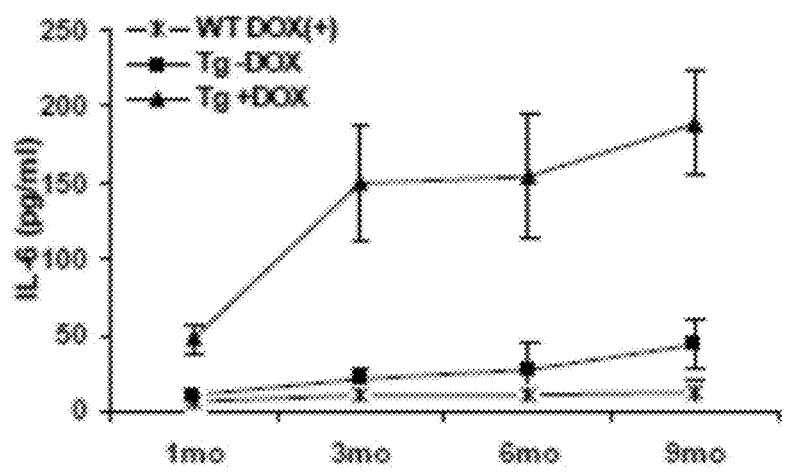
FIG. 5B.—Levels of IL-6 measured in BALF by ELISA after 1, 3, 6 or 9 months of treatment with DOX.
Figure 5C:
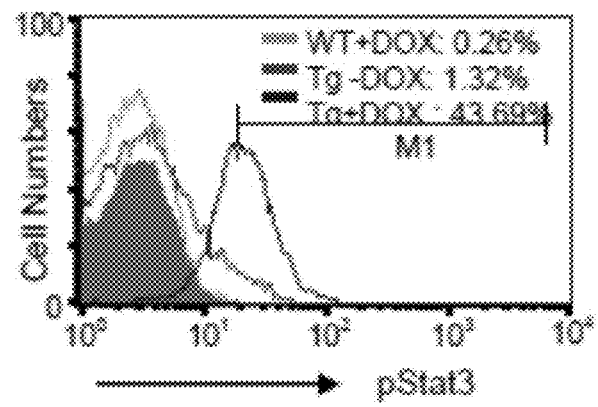
FIG. 5C.—Flow cytometry on lung alveolar type II epithelial cells stained with SP-C and phospho-stat 3.
Figure 5D:
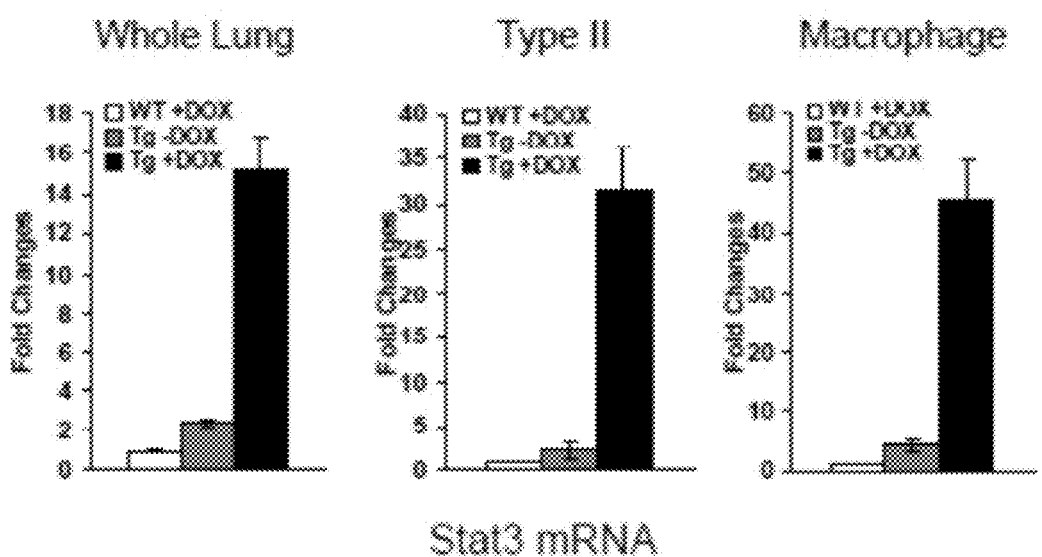
FIG. 5D.—Real-time PCR analysis of stat 3 mRNA expression in whole lung; alveolar macrophages; and alveolar type II epithelial cells from WT and bitransgenic mice treated or untreated with DOX.
Figure 5E:
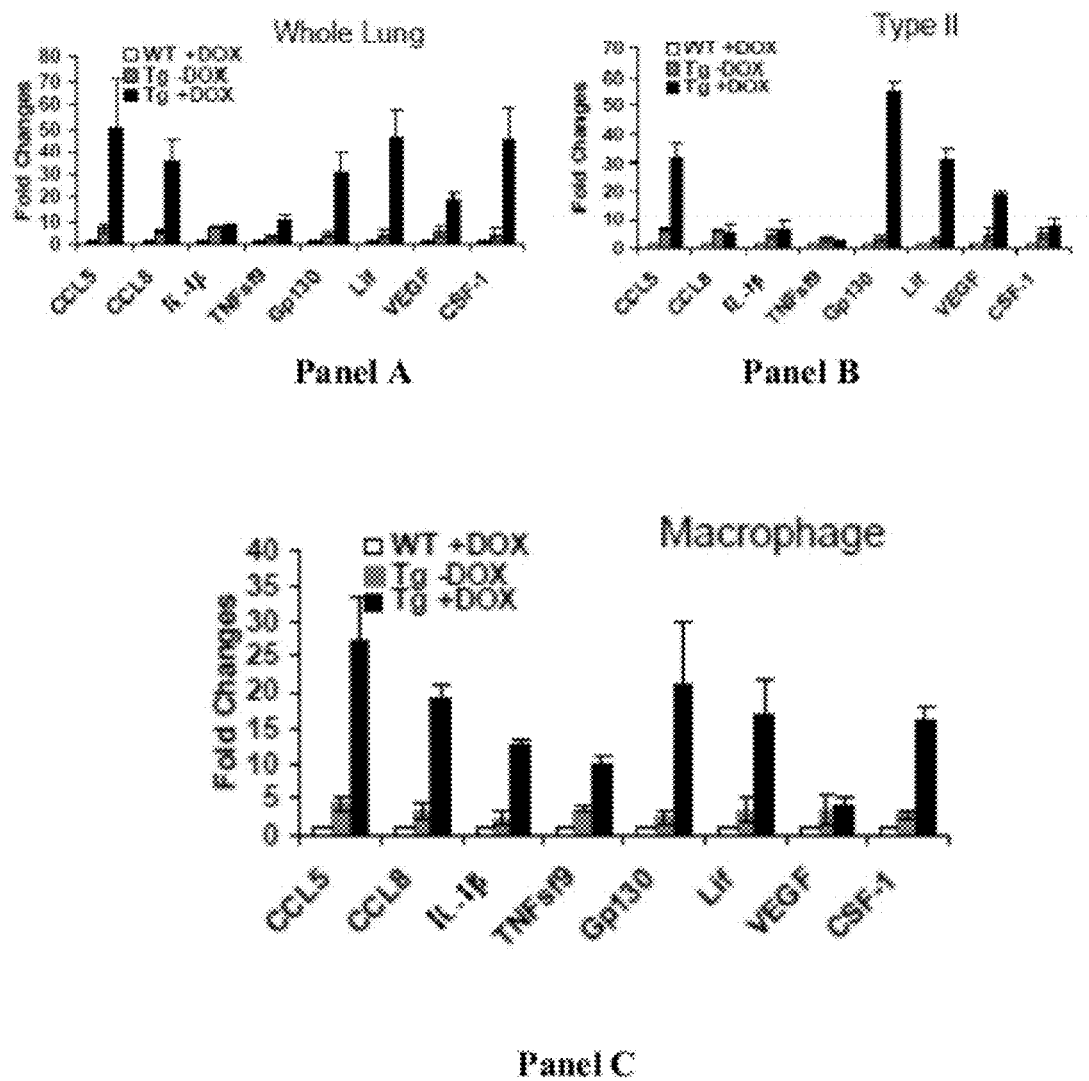
FIG. 5E.—RT-PCR analysis of stat-3 downstream cytokime and Chemokin mRnA express in whole long; alveolar macrophages and alveoler type II epithelial cells (see FIG. 5F).

In the bitransgenic lung, the MMP12 enzymatic activity was significantly increased in the bronchoalveolar lavage fluid (BALF) after doxycyline treatment (FIG. 5A). The concentration of IL-6 was steadily increased in BALF with age progression (FIG. 5B). As a result, activation of pStat3 was observed in alveolar type II epithelial cells of doxycyline-treated bitransgenic mice (FIG. 5C). As previously reported, persistent activation of the Stat3 pathway in these lung epithelial tumor progenitor cells is sufficient to induce bronchioalveolar adenocarcinoma[19]. Stat3 mRNA synthesis was also increased in the whole lung, alveolar type II epithelial cells and bronchioalveolar macrophages from doxycyline-treated bitransgenic mice as measured by Real-Time PCR (FIG. 5D). A group of Stat3 downstream pro-cancer cytokines and chemokines has been identified as we previously reported[19]. Some of these molecules were highly induced in the whole lung, alveolar type II epithelial cells and bronchioalveolar macrophages of doxycyline-treated bitransgenic mice (FIG. 5E). Therefore, myeloid over-expression of MMP12 created a Stat3 pro-tumor microenvironment that favors tumor growth in the lung of bitransgenic mice.

MMP12 Over-Expression Induced Emphysema and Bronchoalveolar Adenocarcinoma in the Lung Referring now to FIG. 6. Over-expression of MMP12 caused MDSCs expansion, emphysema and bronchioalveolar adenocarcinoma in the lung of c-fms-rtTA/(TetO)₇-CMV-MMP12 the bitransgenic mice. FIG. 6A. A representative flow cytometry analysis of Gr-1⁺ and CD11b⁺ cells from the lung of 3-month doxycyline-treated wild type (WT) mice, doxycyline-treated (+DOX) bitransgenic mice and Doxycyline-untreated (−DOX) bitransgenic mice; FIG. 6B Absolute numbers of Gr-1⁺CD11b⁺ cells, Gr-1⁻CD11b⁺ cells and Gr-1⁺CD11b⁻ cells in the lung of 3-, 6-, and 9-month (3 mo, 6 mo, 9 mo) Doxycyline-treated (Tg+DOX), untreated (Tg−DOX) bitransgenic mice, and age-matched Doxycyline-treated wild type mice (WT +DOX). Results are the mean±SD, n>4; FIG. 6C Histological analysis of doxycyline-treated (+DOX) and untreated (−DOX) bitransgenic mice by H&E staining After six weeks of doxycyline treatment (+DOX 6W), emphysema was observed (original magnification×100). Bronchoalveolar adenocarcinomas were found in 4-month (4 M) doxycyline-treated lungs, not in age-matched untreated lungs (original magnification×40). After 9 months (9 M) of Doxycyline treatment, tumor size became grossly identifiable (pointed by green arrow); FIG. 6D Quantitative measurements of alveolar numbers, average mean cord length (Lm), average alveolar surface area and average alveolar volume for emphysema were determined by MetaMorph imaging software. Results are the mean±SD, n=10; FIG. 6A E The lung adenocarcinoma incidence in 4-12 month Doxycyline-treated (+DOX) and untreated bitransgenic mice (−DOX). Thirteen out of 40 Doxycyline-treated mice showed bronchioalveolar adenocarcinoma, and 2 out of 40 untreated mice showed tumor. n=40/group.

Figure 6A:
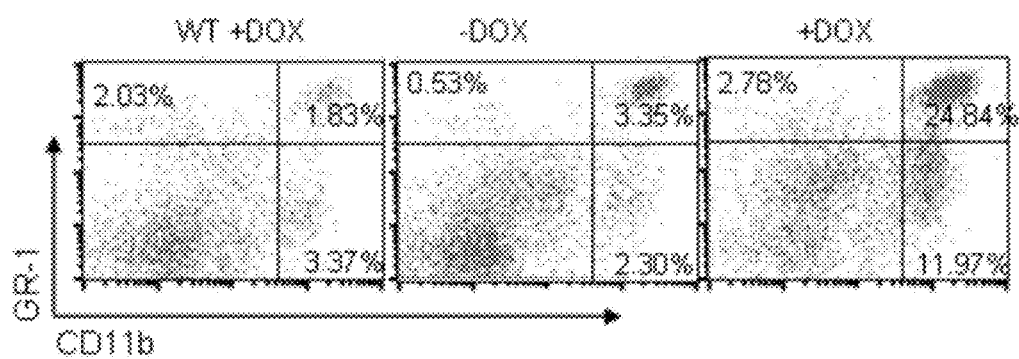
FIG. 6A.—Representative flow cytometry analysis of Gr-1+ and CD116+ cells from lungs of WT and bitransgenic mice treated and untreated with DOX.
Figure 6B:
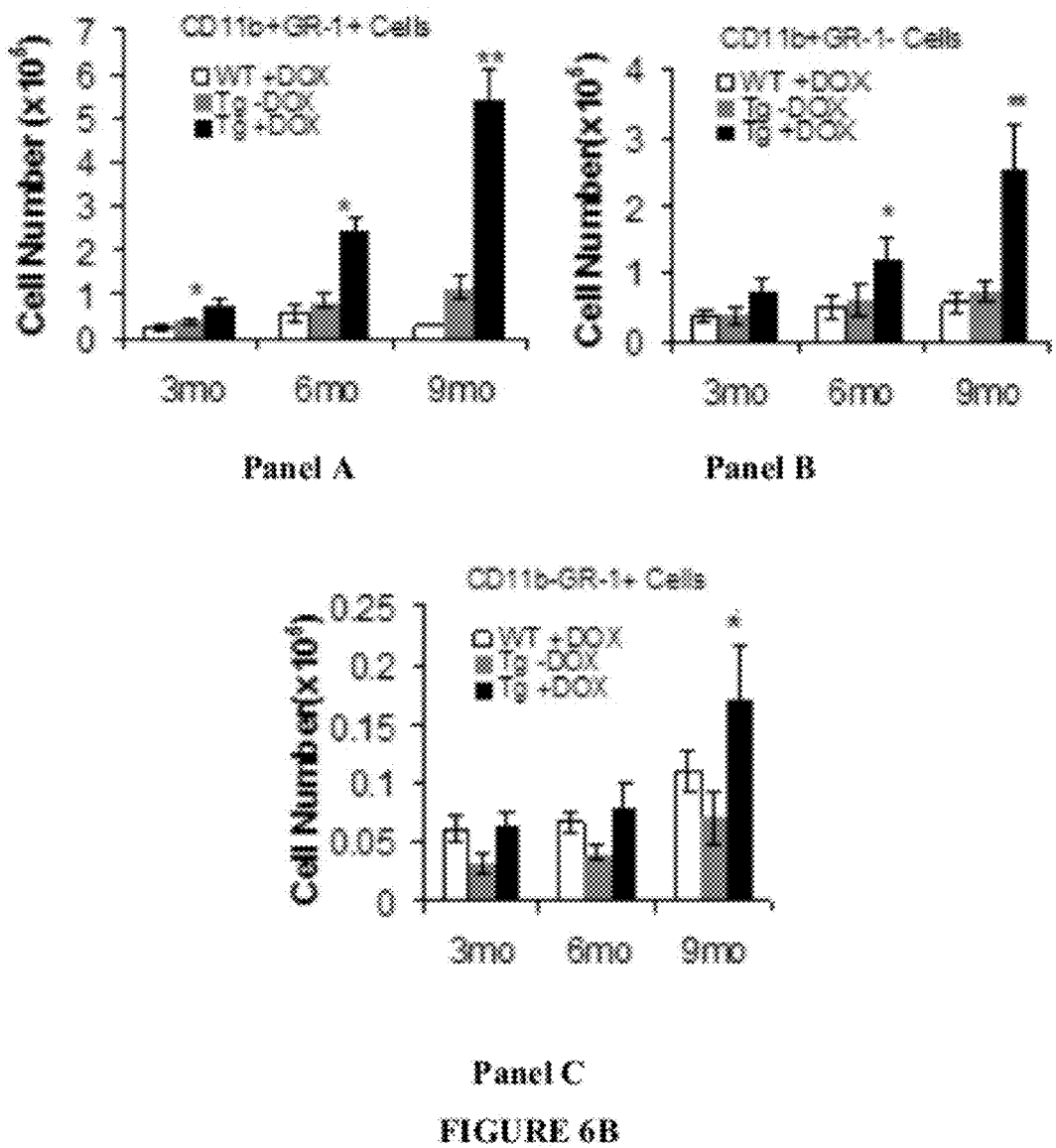
FIG. 6B.—Graph of absolute number of Gr-1+CD11b+ cells, Gr-1-CD11b+ cells; and Gr-1+ CD11b-cells in age matched WT and bitransgenic mice treated and untreated with DOX.
Figure 6C:
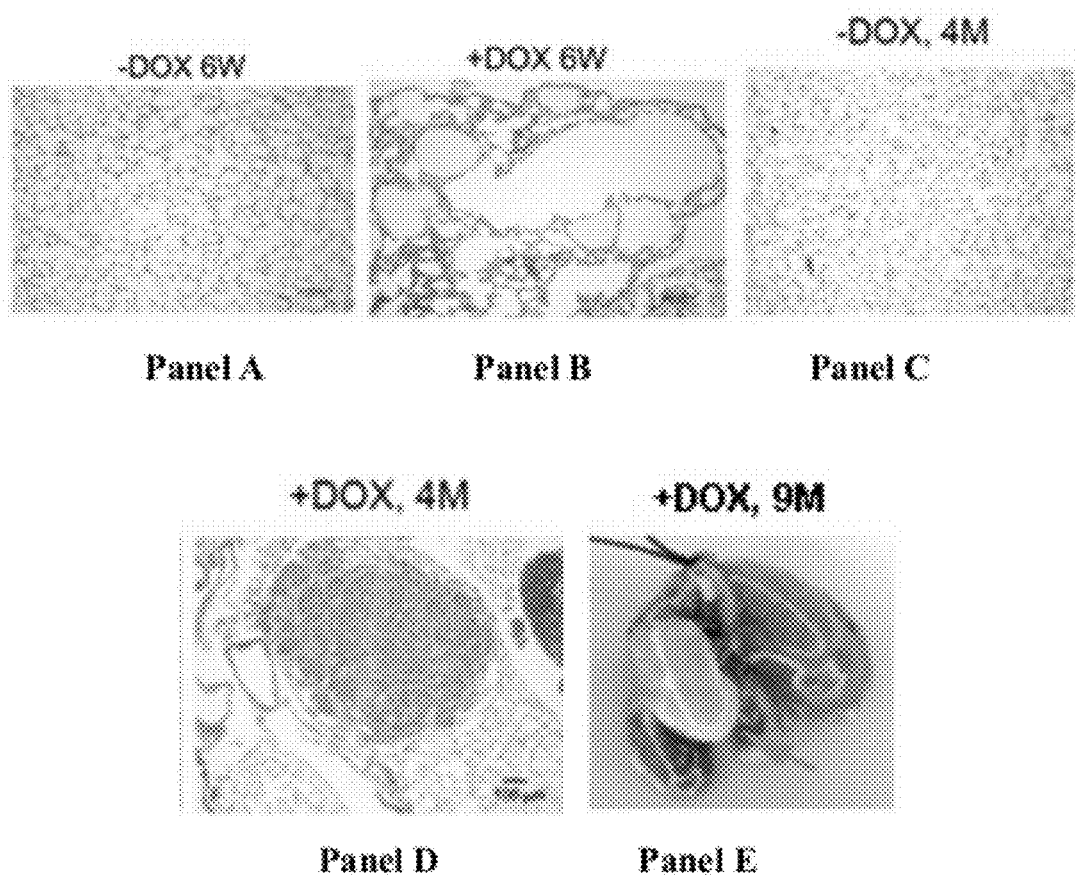
FIG. 6C.—Photomicrographs of H&E stain lung tissue from WT and bitransgenic mice treated with Tg and with or without DOX.
Figure 6D:
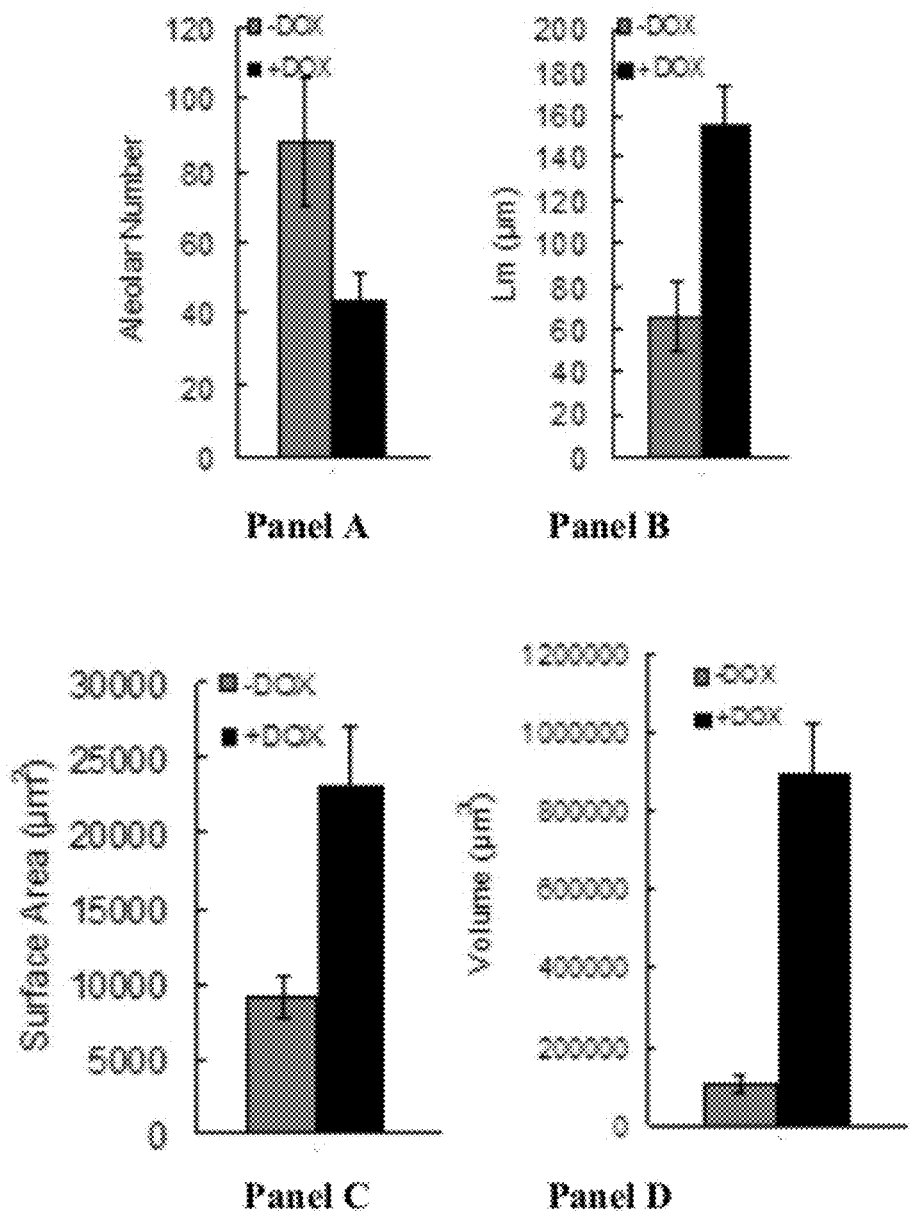
FIG. 6D. Graphs of: alveolar numbers; avenge mean cord length (LM); avenge alveolar surface and volume.
Figure 6E:
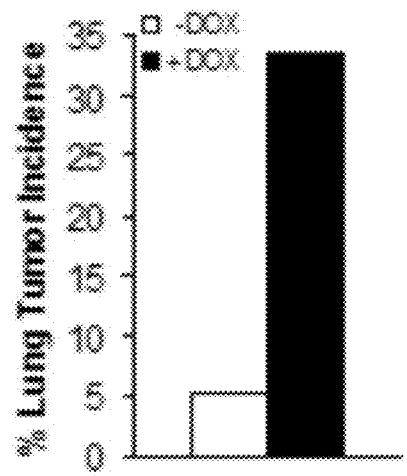
FIG. 6E.—Graph of lung adenocarcinoma incidence in bitransgenic mice treated and untreated with DOX.

Another factor contributing to tumor microenvironment change was MDSCs expansion in the lung of doxycyline-treated bitransgenic mice. Three months after MMP12 induction, the numbers of CD11b⁺/Gr-1⁺ cells were drastically increased in the lung (from 3.35% to 24.84%) compared with those of untreated bitransgenic mice (FIG. 6A). The absolute numbers of CD11b⁺/Gr-1⁺, CD11b⁺ and Gr-1⁺ were all gradually increased in the lung of bitransgenic mice in a time-dependent manner of doxycycline treatment (FIG. 6B). Histopathological analysis revealed that emphysema was developed in the lung after six weeks of doxycycline treatment (FIG. 6C). Quantitative analysis showed that alveolar numbers of doxycycline-treated bitransgenic mice were much less than those of untreated bitransgenic mice. Mean cord length (Lm), alveolar sphere surface area and alveolar volume per average alveolus were all significantly increased in doxycycline-treated bitransgenic mice than in untreated mice (FIG. 6D). After 4 months of doxycycline treatment, multiple animals started to develop+ bronchioalveolar adenocarcinoma in the bitransgenic lung (FIG. 6C). The tumor incidence rate was around 34% in bitransgenic mice after 4-12 months of doxycycline treatment compared with 5% in doxycycline-untreated bitransgenic mice (FIG. 6E).

Bone Marrow Transplantation

Referring now to FIG. 7. Characterization of bone marrow-transplanted chimeric mice FIG. 7A. Flow cytometry analysis of donor myeloid progenitor cells in the bone marrow of bitransgenic (Tg) or wild type (WT) bone marrow-transplanted recipient mice. Tg→WT: bone marrow transplantation from c-fms-rtTA/(TetO)$_7$-CMV-MMP12 bitransgenic mice (CD45.1$^+$) to wild type (CD45.2$^+$) chimeric mice; WT→Tg: bone marrow transplantation from wild type mice (CD45.2$^+$) to bitransgenic (CD45.1$^+$) chimeric mice; +DOX, doxycyline treated; −DOX, doxycycline untreated. n=7-10, *P<0.05; FIG. 7B. Flow cytometry analysis of donor CD11b$^+$ GR-1$^+$ cells from the bone marrow (BM) and spleen of bitransgenic and wild type transplanted chimeric mice, n=7-10, *P<0.05; FIG. 7 C CFSE-labelled wild type CD4$^+$ T cells were stimulated with anti-CD 3 mAb plus anti-CD28 mAb for 3 days in the presence or absence of donor CD45.1$^+$ or CD45.2$^+$ CD11b$^+$Gr-1$^+$ cells isolated from bone marrow transplanted chimeric mice. The ratio between CD11b$^+$Gr-1$^+$ cells:CD4$^+$ T cells was 1:5. Proliferation of labelled CD4$^+$ T cells was analyzed by flow cytometry. Peaks represent cell division cycles; FIG. 7D The concentration of IL-2 in the above cultured medium was measured by ELISA. n=7-10, **P<0.01; FIG. 7E The concentrations of IL-6 and IL-10 were measured from the plasma of bitransgenic and wild type transplanted chimeric mice. n=7-10, *P<0.05, **P<0.01.

Figure 7A:
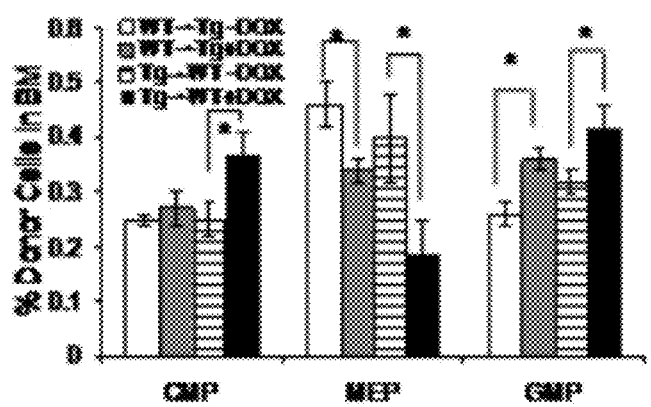
FIG. 7A.—Graph of flow cytometry data of donors myeloid progenitor ator cells in the marrow of bitransgenic (Tg) or (WT) marrow recipient mice.
Figure 7B:
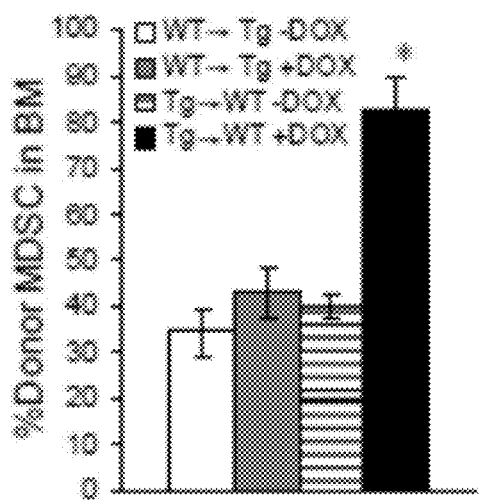
FIG. 7B.—Graphs of flow cytometry data for CD116+GR-1+ cells from marrow (BM) and spleen of transplanted WT and bitransgenic mice.
Figure 7B:
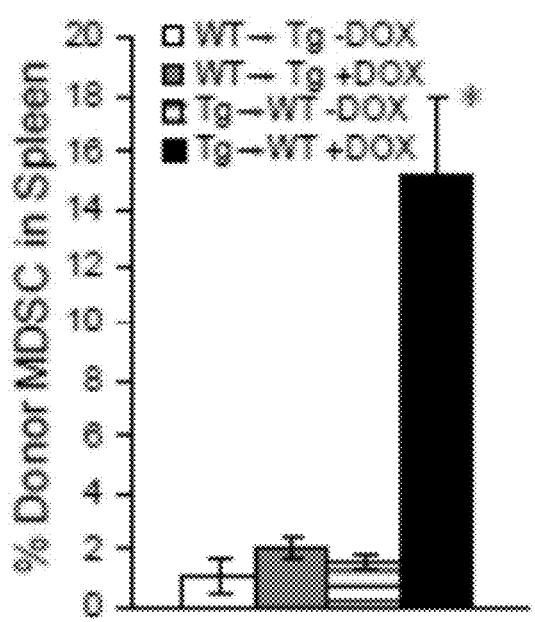
Figure 7C:
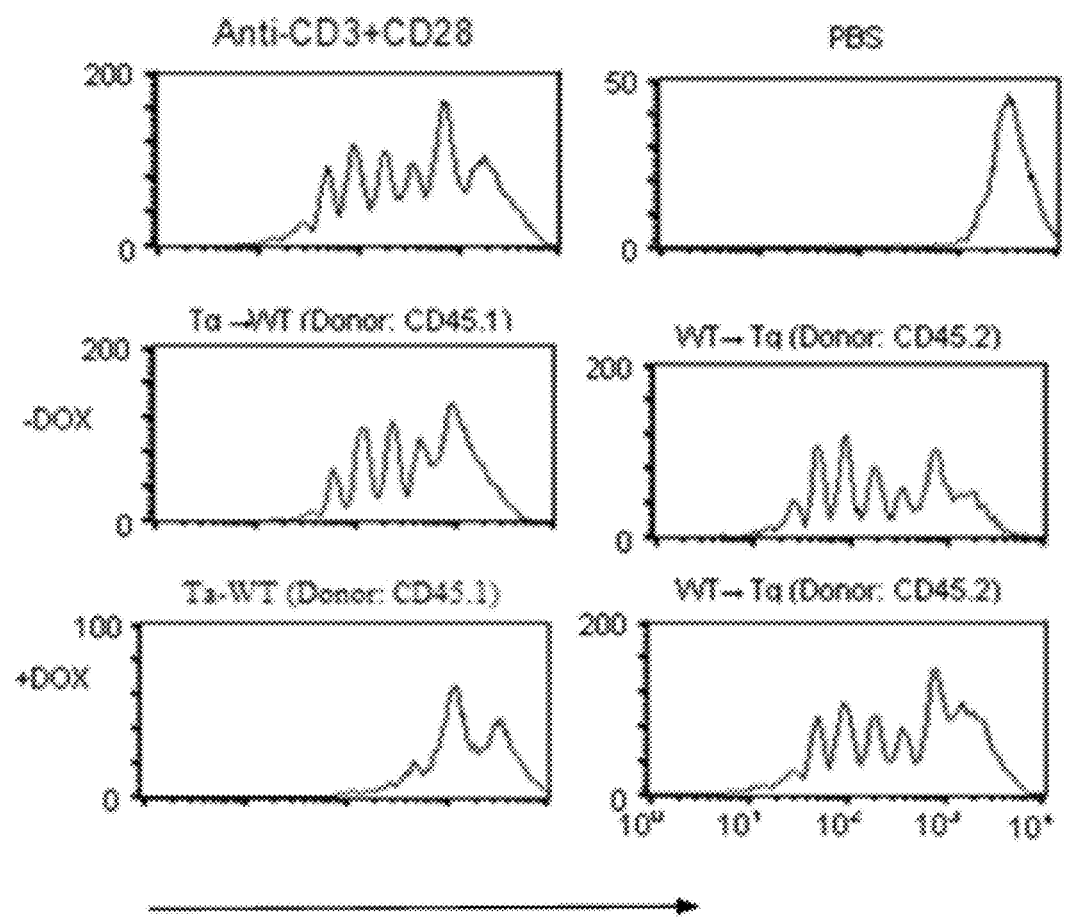
FIG. 7C.—Proliferation of CFSE-labelled WT CD4+ T cells followed by flow cytometry. CD4+ T cells were stimulated with anti CD3 mAb plus anti-CD28 mAb in the presence or absence of donor CD45.1+ or CD45.2+ CD11b+GR-1+ cells from the marrow of transplanted mice.
Figure 7D:
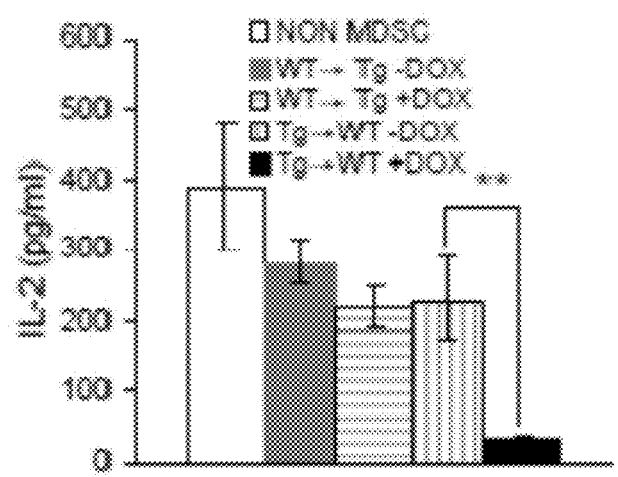
FIG. 7D.—Graph of the concentration of IL-2 in culture media in measure by ELISA.
Figure 7E:
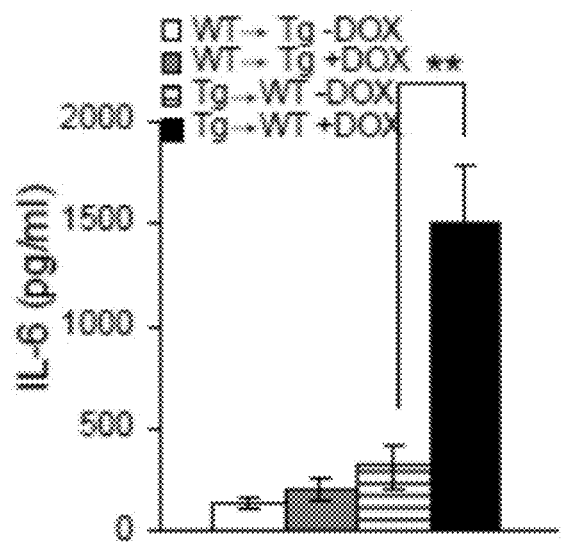
FIG. 7E.—Concentration of IL-6 and IL-1D in the plasma of bitransgenic and WT transplanted chimeric mice.
Figure 7E:
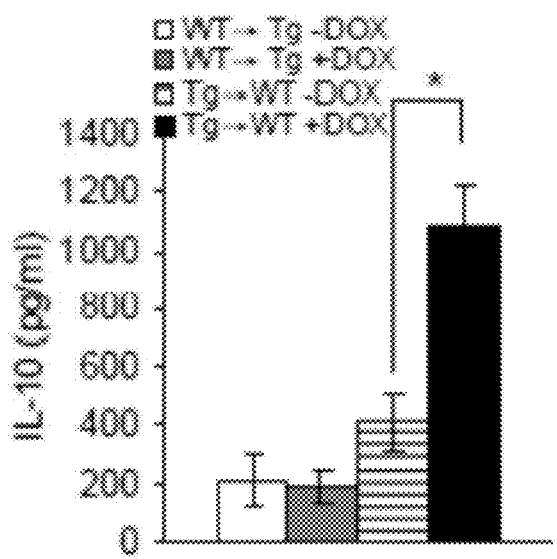

In c-fms-rtTA/(TetO)$_7$-CMV-MMP12 bitransgenic mice, pathological consequences can be caused by MMP12-induced myeloid cell autonomous defect, tissue microenvironment change, or both. To distinguish these mechanisms, bone marrow cells from c-fms-rtTA/(TetO)$_7$-CMV-MMP12 bitransgenic mice (CD45.1) and wild-type mice (CD45.2) were reciprocally transplanted in recipient mice that were lethally irradiated to generate bone marrow chimeric mice. Myeloid cells from donor mice in recipient mice were analyzed by gating with CD45.1 or CD45.2 antigen by flow cytometry. Donor myeloid cells (identified by CD45.1 or CD45.2) in recipient mice were further analyzed. After six-month doxycycline treatment, CMP and GMP donor myeloid progenitor populations (FIG. 7A) and CD11b$^+$/Gr-1$^+$ cells (FIG. 7B) in the bone marrow of wild type mice that were transplanted with the bitransgenic bone marrow cells (Tg→WT +DOX) were higher than those of untreated mice (Tg→WT −DOX). In the spleen, a similar observation was seen with even greater increase of CD11b$^+$/Gr-1$^+$ cells in the same animal groups (FIG. 7B). This suggests that MMP12-induced myeloid autonomous defect contributes to abnormal expansion of myeloid progenitors and CD11b$^+$/Gr-1$^+$ cells. The GMP donor myeloid progenitor population showed abnormal expansion in the bone marrow of bitransgenic mice that were transplanted with the wild type bone marrow cells after a 6-month doxycycline treatment (WT→Tg +DOX) compared with those of untreated mice (WT→Tg −DOX) (FIG. 7A), suggesting a partial contribution of the tissue microenvironment. The CMP and MDSC populations remained relatively unchanged in this study group. Both myeloid autonomous defect and the tissue microenvironment contributed to decrease of the MEP population (FIG. 7A). In the immune suppression assay, CD11b$^+$/Gr-1$^+$ cells from the Tg→WT +DOX group exhibited inhibition of proliferation and function of wild type T cells (FIGS. 7C-D). The expression levels of IL-6 and IL-10 were increased in the plasma of the Tg→WT +DOX group (FIG. 7E). In the Tg→WT +DOX group, 5 out of 10 transplanted mice developed lung carcinoma compared with 1 out of 10 transplanted mice developed lung carcinoma in WT→Tg+DOX group after six months of bone marrow transplantation. In both doxycycline-untreated recipient groups (Tg→WT −DOX, WT→Tg −DOX), no tumor was observed.

One important immune event that provokes inflammation in cancer is CD11b$^+$/Gr-1$^+$ MDSCs expansion[1-3]. In the c-fms-rtTA/(TetO)$_7$-CMV-MMP12 bitransgenic mouse model, this immature immune cell population was dramatically increased in multiple organs (FIGS. 1 and 6) as a result of dysregulated production of myeloid progenitor cells in the bone marrow, in which MMP12 over-expression increased the frequencies and numbers of CMP and GMP while decreased the frequencies and numbers of MEP (FIG. 1). Bone marrow cells from MMP12 over-expressed bitransgenic mice showed a greater potential of forming G-CSF-stimulating colonies (FIG. 1C). These in vivo studies clearly demonstrated that MMP12 has a significant impact on the development, differentiation and commitment of hematopoietic progenitor cells to myeloid lineage cells in the bone marrow, similar to that observed in lysosomal acid lipase (an upstream regulator of MMP12) knock-out mice[15,21]. In the serum, pro-inflammatory cytokines such as IL-10, IL-6, MIP-2 and TNF-α that are known to stimulate MDSCs expansion were highly induced in myeloid MMP12 over-expressing bitransgenic mice in vivo (FIG. 4A). Oncogenic intracellular signaling molecules were highly activated in circulating CD11b$^+$/Gr-1$^+$ cells in multiple organs of bitransgenic mice (FIG. 4B-C and Table 1), an indication of autonomous defect.

The above abnormal hematopoietic activity and CD11b$^+$/Gr-1$^+$ cell expansion can be a direct effect of MMP12 on progenitor cells, or an indirect effect through stimulation of other regulatory pathway loops that exert their effects on bone marrow progenitor cells in vivo. Interestingly, addition of activated-MMP12 was able to stimulate wild type Lin$^-$ progenitor cells to differentiate into the CD11$^+$/Gr-1$^+$ population with characteristics of increased intracellular Stat3, NFκB p65 and CEBP/α activation, and increased IL-6 and IL-10 secretion (FIG. 4D-F), suggesting that MMP12 directly exerts its effect on hematopoietic progenitor cells. This observation was confirmed by in vitro doxycycline treatment of Lin$^-$ progenitor cells from the bone marrow of bitransgenic mice (FIG. 4G-J). Several mechanisms are potentially involved in MMP12-mediated myelopoiesis. MMP12 can cleave various cytokines/chemokines and their membrane-bound receptors to influence myelopoiesis[23]. MMP12 can stimulate myelopoiesis through the non-catalytic domain (e.g. haemopexin-like domain)[24]. MMP12 can also stimulate myelopoiesis through trans-signaling[25]. It is important in the future to elucidate how MMP12 induces inflammation and lung cancer through these mechanisms.

The hallmark signature of CD11b$^+$/Gr-1$^+$ MDSCs is the immunosuppression on proliferation and function of T cells that normally counteract tumor growth[1-3]. In a co-culture experiment, CD11b$^+$/Gr-1$^+$ cells that were isolated from MMP12 over-expressing bitransgenic mice significantly reduced proliferation, lymphokine production and the CD69 expression of CD4$^+$ T cells (FIG. 3C-F) These activities were associated with the increased apoptosis in CD4$^+$ T cells (FIG. 3F). Since both percentage and absolute numbers of Treg cells were increased in doxycycline-treated bitransgenic mice (FIG. 2B), it represents the second mechanism for reduction of CD4$^+$ T proliferation and function. It is known that Treg cells inhibit CD4$^+$ T cells in cancer[26]. Interestingly and importantly, MMP12 showed a direct inhibitory effect on proliferation and function of T cells in the in vitro study (FIG.

2E-F). Again, these suppressive activities can be mediated through MMP12 shedding, haemopexin-like domain and trans-signaling as outlined above. Therefore, in c-fms-rtTA/(TetO)$_7$-CMV-MMP12 bitransgenic mice, over-expression of MMP12 suppresses CD4$^+$ T cells through at least three mechanisms: 1) promoting CD11b$^+$/Gr-1$^+$ MDSCs; 2) increasing Treg cells; 3) directly inhibiting CD4$^+$ T cells.

In the distal organs, macrophage-secreted MMP12 is well known for its pathogenic function in the lung. In doxycycline-treated bitransgenic mice, in addition to promoting expression/activation of IL-6 and Stat3 in CD11b$^+$/Gr-1$^+$ cells of the lung (FIG. 6), MMP12 over-expression stimulated expression and activation of Stat3 and its downstream genes in lung tumor progenitor epithelial cells (e.g. AT II epithelial cells) (FIG. 5). As reported previously, persistent activation of Stat3 and its downstream genes in alveolar type II epithelial cells causes chronic inflammation and bronchioalveolar adenocarcinomas[19]. Therefore, both immune and non-immune events in doxycycline-treated bitransgenic mice resulted in local microenvironment changes in the lung that favored tumor growth. Indeed, sequential formation of emphysema and bronchioalveolar adenocarcinoma was observed in doxycycline-treated bitransgenic lung (FIG. 6). This resembles the recent discovery in which MMP12 over-expression in lung epithelial cells caused emphysema and bronchioalveolar adenocarcinoma[11]. It is known that human COPD patients are a population at high risk of developing lung cancer. Our observations mimic clinical smoking-induced COPD (the major phenotype is emphysema) and lung cancer in humans, and provide a mechanistic connection between two diseases.

Since CD11b$^+$/Gr-1$^+$ MDSCs expansion is originated from malformation of progenitor cells in the bone marrow, it is necessary to determine whether bronchioalveolar adenocarcinoma is due to MMP12-induced myeloid autonomous defect. The myeloid cell autonomous defect was evidenced by abnormal activation of multi-intracellular signaling molecules as a result of MMP12 over-expression (FIG. 4B, C and Table 1). In the bone marrow transplantation study, defective myeloid lineage progenitor cells were sufficient to induce CMP/GMP malformation, CD11b$^+$/Gr-1$^+$ population expansion, T cell suppression and tumorigenesis in the lung of recipient wild type mice (FIG. 7). Tissue microenvironment also contributes to tumor formation although at a much lower rate (1/10 mice) compared with the myeloid autonomous effect (5/10 mice).

In summary, a critical role of MMP12 in the transition from emphysema to lung cancer was demonstrated. The process was initiated from the abnormal development of hematopoietic progenitor cells that skew toward expansion of myeloid lineage cells. This caused systemic CD11b$^+$/Gr-1$^+$ MDSCs expansion, increase of Treg cells and up-regulation of pro-inflammatory cytokines/chemokines This inflammatory environment change hijacked immune surveillance by inhibiting T cell proliferation and function. In addition, MMP12 over-expression induced non-immune responses by activating the oncogenic Stat3 pathway in tumor progenitor epithelial cells. Besides its function of extracellular matrix degradation for tumor growth and metastasis, the results demonstrate new functions were revealed for MMP12 in this report. Taken together, MMP12 is a pleiotrophic molecule in hematopoiesis, myelopoiesis, immune suppression, tissue remodeling and tumorigenesis.

Materials and Methods

Animal Care

All scientific protocols involving the use of animals have been approved by the Institutional Animal Care and Use Committee (IACUC) of Indiana University School of Medicine and followed guidelines established by the Panel on Euthanasia of the American Veterinary Medical Association. Protocols involving the use of recombinant DNA or biohazardous materials have been approved by the Biosafety Committee of Indiana University School of Medicine and followed guidelines established by the National Institutes of Health. Animals were housed under (IACUC)-approved conditions in a secure animal facility at Indiana University School of Medicine.

Generation of Doxycycline-Controlled MMP12 Transgenic Mouse Line

The (TetO)$_7$-CMV-MMP12 transgenic mouse line and the c-fms-rtTA transgenic mouse line were generated and genotyped as previously reported[11,12]. C-fms-rtTA/(TetO)$_7$-CMV-MMP12 bitransgenic mice were obtained by crossbreeding C-fms-rtTA and (TetO)$_7$-CMV-MMP12 transgenic mice. To distinguish closed MMP12 from endogenous MMP12, a Flag sequence was inserted at the C-terminus of MMP12 in bitransgenic mice to allow detection of MMP12-Flag fusion protein expression by anti-Flag antibody as we previously described[11].

Fluorescence Activated Cell Sorting (FACS) Analysis

Bone marrow, spleen and lung single cell suspensions were prepared as previously described[13]. For 6-color hematopoietic progenitor analysis and sorting[14], a previously described procedure was used[15]. Lineage markers (biotin-CD3, -CD4, -CD8, -Mac-1, -Gr-1, -Ter119, and -B220) and other marker antibodies (Sca-1, c-Kit, IL7Rα, and CD34) were purchased from BD Biosciences (San Jose, Calif.). Anti-CD16/32 (93), anti-CD11c (N148), anti-CD11b (M1/70), anti-Gr-1 (RB6-8c5), anti-CD4 (GK1.5), anti-CD 45.1 (A20), anti-CD45.2 (104) anti-CD8 (53-6.7) and anti-B220 (RA3-6B2) were purchased from e-Biosciences (San Diego, Calif.). The measurement of intracellular signaling molecules was performed according to the protocols previously described[13]. Anti-phospho-Erk1/2, P38, NFkB, Stat1 and Stat3 were purchased from Cell Signaling Technology (Danvers, Mass.). Anti-MMP12 antibody was used in combination with the above lineage markers to measure MMP12 protein expression in lal−/− myeloid lineage progenitor cells. Samples were analyzed on a LSRII machine (BD Biosciences). Percentage cell numbers and mean fluorescence intensity (MFI) were analyzed using the BD FACStation™ Software (BD Biosciences). Quadrants were assigned using isotype control.

Methylcellulose Colony Forming Assays

For the G-CSF dependent CFU (CFU-G) assay a previous procedure was used[15].

MMP-12 Activity Assay

The MMP-12 specific activity from the serum and bronchioalveolar lavage fluid (BALF) was measured by the SensoLyte™ 490 MMP-12 Assay Kit (AnaSpec, San Jose, Calif., USA)[11].

Alveolar Type II Epithelial Cell Purification

Alveolar type II epithelial cells were purified from wild type mice, doxycycline treated or untreated bitransgenic mice as described previously[16 17 18].

Histology

The lungs from doxycycline-treated or untreated c-fms-rtTA/(TetO)$_7$-CMV-MMP12 bitransgenic mice were inflated with a fixative solution (4% paraformaldehyde, 1× phosphate-buffered saline) and dissected out and stored in fixative at 4° C. for 24 hours. After fixation and embedding in paraffin, tissue sections were cut to 5 µm thick. Multiple sections from each lung were stained with hematoxylin and eosin. Tumor incidence and multiplicity in each section were counted.

Real Time PCR

Real-Time PCR analysis was performed as previously described[19] using the Taqman Reverse Transcription Kit and SYBR Green PCR Master Mix (Applied Biosystems, Foster City, Calif.). GAPDH primers were used as an endogenous control for normalizing all cDNA samples. The reactions were analyzed using the StepOne Plus Real-Time PCR System (Applied Biosystems).

```
Primers for Real-Time PCR:
mCCL5
                                    SEQ ID NO. 1.
Upstream:    5'-GGAGTATTTCTACACCAGCAGCAA-3'
                                    SEQ ID NO. 2.
Downstream:  5'-CGGTTCCTTCGAGTGACAAAC-3' mCCL8
                                    SEQ ID NO. 3.
Upstream:    5'-AAAGCTACGAGAGAATCAACAATATCC-3'
                                    SEQ ID NO. 4.
Downstream:  5'-CCTGCTTGGTCTGGAAAACC-3'

CSF-1
                                    SEQ ID NO. 5.
Upstream:    5'-TCCAATAACCTGAACAGCTGCTT-3'
                                    SEQ ID NO. 6.
Downstream:  5'-AGTTCGGACACAGGCCTTGT-3' mGP130
                                    SEQ ID NO. 7.
Upstream:    5'-CCCATGGGCAGGAATATAGATC-3'
                                    SEQ ID NO. 8.
Downstream:  5'-TTCCCATTGGCTTCAGAAAGA-3' mIL-1β
                                    SEQ ID NO. 9.
Upstream:    5'-TTGACGGACCCCAAAAGATG-3'
                                    SEQ ID NO. 10.
Downstream:  5'-CAGGACAGCCCAGGTCAAA-3' mIL-6
                                    SEQ ID NO. 11.
Upstream:    5'-GAGGCTTAATTACACATGTTC-3'
                                    SEQ ID NO. 12.
Downstream:  5'-TGCCATTGCACAACTCTTTTCT-3' mLif
                                    SEQ ID NO. 13.
Upstream:    5'-GAGTCCAGCCCATAATGAAGGT-3'
                                    SEQ ID NO. 14.
Downstream:  5'-GTGCAGAACCAGCAGCAGTAAG-3' mMMP-12
                                    SEQ ID NO. 15.
Upstream:    5'-TGGTATTCAAGGAGATGCACATTT-3'
                                    SEQ ID NO. 16.
Downstream:  5'-GGTTTGTGCCTTGAAAACTTTTAGT-3' mTNFsf9
                                    SEQ ID NO. 17.
Upstream:    5'-CGCCAAGCTACTGGCTAAAAA-3'
                                    SEQ ID NO. 18.
Downstream:  5'-GGCTGTGCCAGTTCAGAGTTG-3' mVEGF
                                    SEQ ID NO. 19.
Upstream:    5'-CCCACGTCAGAGAGCAACATC-3'
                                    SEQ ID NO. 20.
Downstream:  5'-TGGCTTTGGTGAGGTTTGATC-3'
```

CD11b$^+$/Gr-1$^+$ Cell Purification

Bone marrow or spleen cells were placed in anti-CD11b Ab-coated culture dishes and incubated for 3 hours at 37° C. in 5% $CO_2$. Cells were gently washed with PBS to remove the plastic nonadherent cells. Adherent cells were incubated with biotin-labelled primary GR-1 antibody for 20 minutes, followed by a 20 minute incubation of anti-biotin secondary antibody beads in PBS. Labelled cells were selected on a MS column using magnetic-activated cell sorting technology (Miltenyi Biotech Inc, Auburn, Calif.).

In Vitro MDSC Suppression Assay

CD4$^+$ T cells were isolated with CD4$^+$ monoclonal antibody-coated magnetic beads and MACS-LS columns according to the manufacturer's instructions (Miltenyi Biotec, Auburn, Calif.) and CFSE labelled. Labelled cells were stimulated with anti-CD3 mAb plus anti-CD28 mAb for 3 days in the presence or absence of CD11b$^+$/Gr-1$^+$ cells that were isolated from the spleens of wild type mice, doxycycline-treated or untreated c-fms-rtTA/(TetO)$_7$-CMV-MMP12 bitransgenic mice. The ratio between CD11b$^+$/Gr-1$^+$ MDSCs: CD4$^+$ T cells was 1:5. Proliferation of CD4$^+$ T cells was evaluated as CFSE dilution by flow cytometry. T cell activation was monitored with anti-CD69 antibody as previously described[15].

In Vitro Treg Suppression Assay

CD4$^+$/CD25$^+$ T cells were isolated from the spleens of wild type mice, doxycycline-treated or untreated c-fms-rtTA/(TetO)$_7$-CMV-MMP12 bitransgenic mice by CD4$^+$/CD25$^+$ T Cell Isolating Kit and MACS-LS columns according to the manufacturer's instructions (Miltenyi Biotec, Auburn, Calif.). CFSE-labelled CD4$^+$ T cell suppression was performed as outlined above. The ratio between Treg: CD4$^+$ T cells in co-culture was 1:1.

Cytokine Measurement by ELISA

To measure cytokine and lymphokine concentrations, the blood plasma and cultured medium were harvested and measured using OptEIA ELISA kits for mouse IFN-γ, IL-2, IL-4, IL-6, IL-10, MIP-2 and TGF-β according to the manufacturer's instructions (R&D Systems, Minneapolis, Minn.).

Lin$^-$ Bone Marrow Cell Isolation

Bone marrow cells were isolated from wild-type mice (8 to 10 weeks of age). Erythrocytes were lysed and Lin$^-$ bone marrow cells were isolated by removing blood lineage marker-positive cells with an immunomagnetic microbead technique. Briefly, bone marrow cells were labelled with a cocktail of biotin-coupled antibodies raised against lineage-specific antigens: CD11b, GR-1, B220, TER-119, and CD3ε (Mouse Lineage panel Kit; BD Pharmingen, San Diego, Calif.). Following a 20 min incubation with biotin-labelled primary antibodies at 4° C., unlabelled cells were separated on a depletion column using magnetic-activated cell sorting technology according to the manufacturer's instruction (Miltenyi Biotech, Auburn, Calif.).

In Vitro MMP12 Study

MMP12 was activated by incubation of rmMMP12 (R&D System) with p-aminophenylmercuric acetate (APMA) (1 mM) for 1 hour. For the progenitor cell differentiation study, Lin$^-$ progenitor cells were purified from the bone marrow of wild type mice. Inactivated and APMA-activated-MMP12 were added to in vitro cultured Lin$^-$ bone marrow cells (200 μl) at 1, 5 and 10 ng/ml for 1, 3, 6 hours. After culturing, cells were stained with CD11b$^+$, Gr-1$^+$, pStat3, C/EBPα and pNFκB antibodies for flow cytometry analysis. The concentrations of IL-10 and IL-6 were measured in the medium using ELISA kit (BD Bioscience, San Diego, Calif.).

For the CD4$^+$ T cell study, isolated CD4$^+$ T cells were incubated with or without anti-CD3 plus anti-CD28 monoclonal antibodies (mAb) in the presence of inactivated-MMP12 or APMA-activated-MMP12. After three days, activation of cultured T cells was analyzed with CD69 expression by flow cytometry. The concentrations of IL-2, IL-4 and IFN-γ in the medium were measured using an ELISA kit (BD Bioscience).

For doxycycline inducible in vitro studies, Lin$^-$ bone marrow cells or CD4$^+$ T cells from wild type or bitransgenic mice were cultured in vitro with or without doxycycline at 60 µg/ml. After three days, cultured cells were harvested and stained with appropriate antibodies. Supernatants were harvested for cytokine measurement by ELISA.

Bone Marrow Chimera Mice

The bone marrow was flushed from the femurs and tibias of 8 to 10-week-old donor c-fms-rtTA/(TetO)$_7$-CMV-MMP12 bitransgenic mice or wild-type mice. Mature lymphocytes were depleted from the bone marrow cell preparation using CD4 and CD8 antibody-linked magnet-activated cell sorting (Miltenyi Biotech, Auburn, Calif.). These donor cells were referred to as T cell-depleted bone marrow cells. Three-month old recipient c-fms-rtTA/(TetO)$_7$-CMV-MMP12 bitransgenic mice or wild-type mice were lethally irradiated with 1000 rad of γ-irradiation and rested 1 day before receiving 2.5 to 5×10$^6$ T cell-depleted bone marrow cells in 500 µl 1×PBS via tail vein. Reconstituted mice were analyzed six months later.

Statistical Analysis

The data were mean values of at least three independent experiments and expressed as the mean±SD. A paired Student's t test or ANOVA was used to evaluate the significance of the differences. Statistical significance was set at a level of P<0.05.

REFERENCES

1. Sica A, Bronte V. *Altered macrophage differentiation and immune dysfunction in tumor development.* J Clin Invest. 2007; 117(5):1155-1166.
2. Ostrand-Rosenberg S, Sinha P. *Myeloid-derived suppressor cells: linking inflammation and cancer.* J. Immunol. 2009; 182(8):4499-4506.
3. Gabrilovich D I, Nagaraj S. *Myeloid-derived suppressor cells as regulators of the immune system.* Nat Rev Immunol. 2009; 9(3):162-174.
4. Page-McCaw A, Ewald A J, Werb Z. *Matrix metalloproteinases and the regulation of tissue remodelling.* Nat Rev Mol Cell Biol. 2007; 8(3):221-233.
5. Kessenbrock K, Plaks V, Werb Z. *Matrix metalloproteinases: regulators of the tumor microenvironment.* Cell 2010 (1); 141:52-67.
6. Werb Z, Gordon S. *Elastase secretion by stimulated macrophages. Characterization and regulation.* J Exp Med. 1975; 142(2):361-377.
7. Gronski T J, Jr., Martin R L, Kobayashi D K, et al. *Hydrolysis of a broad spectrum of extracellular matrix proteins by human macrophage elastase.* J Biol. Chem. 1997; 272(18): 12189-12194.
8. Shapiro S D, Kobayashi D K, Ley T J. *Cloning and characterization of a unique elastolytic metalloproteinase produced by human alveolar macrophages.* J Biol. Chem. 1993; 268(32):23824-23829.
9. Hautamaki R D, Kobayashi D K, Senior R M, Shapiro S D. *Requirement for macrophage elastase for cigarette smoke-induced emphysema in mice.* Science. 1997; 277(5334): 2002-2004.
10. Hofmann H S, Hansen G, Richter G, et al. *Matrix metalloproteinase-12 expression correlates with local recurrence and metastatic disease in non-small cell lung cancer patients.* Clin Cancer Res. 2005; 11(3):1086-1092.
11. Qu P, Du H, Wang X, Yan C. *Matrix metalloproteinase 12 overexpression in lung epithelial cells plays a key role in emphysema to lung bronchioalveolar adenocarcinoma transition.* Cancer Res. 2009; 69(18):7252-7261.
12. Yan C, Lian X, Li Y, et al. *Macrophage-Specific Expression of Human Lysosomal Acid Lipase Corrects Inflammation and Pathogenic Phenotypes in lal-/- Mice.* Am J. Pathol. 2006; 169(3):916-926.
13. Qu P, Du H, Li Y, Yan C. *Myeloid-specific expression of Api6/AIM/Sp alpha induces systemic inflammation and adenocarcinoma in the lung.* J. Immunol. 2009; 182(3): 1648-1659.
14. Weissman I L, Shizuru J A. *The origins of the identification and isolation of hematopoietic stem cells, and their capability to induce donor-specific transplantation tolerance and treat autoimmune diseases.* Blood. 2008; 112(9): 3543-3553.
15. Qu P, Shelley W C, Yoder M C, Wu L, Du H, Yan C. *Critical roles of lysosomal acid lipase in myelopoiesis.* Am J. Pathol. 2010; 176(5):2394-2404.
16. Rice W R, Conkright J J, Na C L, Ikegami M, Shannon J M, Weaver T E. *Maintenance of the mouse type II cell phenotype in vitro.* Am J Physiol Lung Cell Mol. Physiol. 2002; 283(2):L256-264.
17. Yang L, Lian X, Cowen A, Xu H, Du H, Yan C. *Synergy between signal transducer and activator of transcription 3 and retinoic acid receptor-alpha in regulation of the surfactant protein B gene in the lung.* Mol. Endocrinol. 2004; 18(6):1520-1532.
18. Yan C, Lian X, Dai Y, et al. *Gene delivery by the hSP-B promoter to lung alveolar type II epithelial cells in LAL-knockout mice through bone marrow mesenchymal stem cells.* Gene Ther. 2007; 14(20):1461-1470.
19. Li Y, Du H, Qin Y, Roberts J, Cummings O W, Yan C. *Activation of the signal transducers and activators of the transcription 3 pathway in alveolar epithelial cells induces inflammation and adenocarcinomas in mouse lung.* Cancer Res. 2007; 67(18):8494-8503.
20. Lian X, Yan C, Yang L, Xu Y, Du H. *Lysosomal acid lipase deficiency causes respiratory inflammation and destruction in the lung.* Am J Physiol Lung Cell Mol. Physiol. 2004; 286(4):L801-807.
21. Lian X, Yan C, Qin Y, Knox L, Li T, Du H. *Neutral lipids and peroxisome proliferator-activated receptor-{gamma} control pulmonary gene expression and inflammation-triggered pathogenesis in lysosomal acid lipase knockout mice.* Am J. Pathol. 2005; 167(3):813-821.
22. Jha P. *Avoidable global cancer deaths and total deaths from smoking.* Nat Rev Cancer. 2009; 9(9):655-664.
23. Dean R A, Cox J H, Bellac C L, Doucet A, Starr A E, Overall C M. *Macrophage-specific metalloelastase (MMP-12) truncates and inactivates ELR+CXC chemokines and generates CCL2, -7, -8, and -13 antagonists: potential role of the macrophage in terminating polymorphonuclear leukocyte influx.* Blood. 2008; 112(8):3455-3464.
24. Houghton A M, Hartzell W O, Robbins C S, Gomis-Ruth F X, Shapiro S D. *Macrophage elastase kills bacteria within murine macrophages.* Nature. 2009; 460(7255):637-641.
25. Chalaris A, Gewiese J, Paliga K, et al. *ADAM17-mediated shedding of the IL6R induces cleavage of the membrane stub by gamma-secretase.* Biochim Biophys Acta; 1803 (2):234-245.
26. Wang H Y, Wang R F. *Regulatory T cells and cancer.* Curr Opin Immunol. 2007; 19(2):217-223.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A transgenic mouse, comprising:
a c-fms-rtTA(TetO)$_7$-CMV-MMP12 transgene stably integrated into the genome of the mouse, wherein said mouse exhibits abnormal development and differentiation of bone marrow progenitor cells and an elevated tendency to develop lung tumors and/or emphysema.

2. The transgenic mouse according to claim 1, wherein said mouse expresses matrix metalloproteinase 12 specifically in myeloid lineage cells upon treatment with doxycycline.

3. The transgenic mouse according to claim 2, wherein said mouse expresses matrix metalloproteinase 12 with the concentration of at least 2000 ng $\mu L^{-1}$ in plasma.

4. A screening method comprising the steps of:
contacting the transgenic mouse of claim 1 with a reagent, and
observing changes in the development or differentiation of bone marrow progenitor cells or tendency to develop tumors and/or emphysema.

5. The method according to claim 4, wherein said reagent is a small molecule.

6. The method according to claim 4, wherein said reagent is a biologic.

7. The method of claim 4, wherein the reagent is an inhibitor of MMP12.

* * * * *

```
                         SEQUENCE LISTING

<160> NUMBER OF SEQ ID NOS: 20

<210> SEQ ID NO 1
<211> LENGTH: 24
<212> TYPE: DNA
<213> ORGANISM: Artificial
<220> FEATURE:
<223> OTHER INFORMATION: mCCL5 Upstream Primer

<400> SEQUENCE: 1
ggagtatttc tacaccagca gcaa                                          24

<210> SEQ ID NO 2
<211> LENGTH: 21
<212> TYPE: DNA
<213> ORGANISM: Artificial
<220> FEATURE:
<223> OTHER INFORMATION: mCCL5 Downstream Primer

<400> SEQUENCE: 2
cggttccttc gagtgacaaa c                                             21

<210> SEQ ID NO 3
<211> LENGTH: 27
<212> TYPE: DNA
<213> ORGANISM: Artificial
<220> FEATURE:
<223> OTHER INFORMATION: mCCL8 Upstream Primer

<400> SEQUENCE: 3
aaagctacga gagaatcaac aatatcc                                       27

<210> SEQ ID NO 4
<211> LENGTH: 20
<212> TYPE: DNA
<213> ORGANISM: Artificial
<220> FEATURE:
<223> OTHER INFORMATION: mCCL8 Downstream Primer

<400> SEQUENCE: 4
cctgcttggt ctggaaaacc                                               20

<210> SEQ ID NO 5
<211> LENGTH: 23
<212> TYPE: DNA
<213> ORGANISM: Artificial
<220> FEATURE:
<223> OTHER INFORMATION: CSF-1 Upstream Primer

<400> SEQUENCE: 5
tccaataacc tgaacagctg ctt                                           23

<210> SEQ ID NO 6
<211> LENGTH: 20
<212> TYPE: DNA
<213> ORGANISM: Artificial
<220> FEATURE:
<223> OTHER INFORMATION: CSF-1 Downstream Primer

<400> SEQUENCE: 6
agttcggaca caggccttgt                                               20
```

```
<210> SEQ ID NO 7
<211> LENGTH: 22
<212> TYPE: DNA
<213> ORGANISM: Artificial
<220> FEATURE:
<223> OTHER INFORMATION: mGP130 Upstream Primer

<400> SEQUENCE: 7
cccatgggca ggaatataga tc                                              22

<210> SEQ ID NO 8
<211> LENGTH: 21
<212> TYPE: DNA
<213> ORGANISM: Artificial
<220> FEATURE:
<223> OTHER INFORMATION: mGP130 Downstream Primer

<400> SEQUENCE: 8
ttcccattgg cttcagaaag a                                               21

<210> SEQ ID NO 9
<211> LENGTH: 20
<212> TYPE: DNA
<213> ORGANISM: Artificial
<220> FEATURE:
<223> OTHER INFORMATION: mIL-1beta Upstream Primer

<400> SEQUENCE: 9
ttgacggacc ccaaaagatg                                                 20

<210> SEQ ID NO 10
<211> LENGTH: 19
<212> TYPE: DNA
<213> ORGANISM: Artificial
<220> FEATURE:
<223> OTHER INFORMATION: mIL-1beta Downstream Primer

<400> SEQUENCE: 10
caggacagcc caggtcaaa                                                  19

<210> SEQ ID NO 11
<211> LENGTH: 21
<212> TYPE: DNA
<213> ORGANISM: Artificial
<220> FEATURE:
<223> OTHER INFORMATION: mIL-6 Upstream Primer

<400> SEQUENCE: 11
gaggcttaat tacacatgtt c                                               21

<210> SEQ ID NO 12
<211> LENGTH: 22
<212> TYPE: DNA
<213> ORGANISM: Artificial
<220> FEATURE:
<223> OTHER INFORMATION: mIL-6 Downstream Primer

<400> SEQUENCE: 12
tgccattgca caactctttt ct                                              22

<210> SEQ ID NO 13
<211> LENGTH: 22
<212> TYPE: DNA
<213> ORGANISM: Artificial
<220> FEATURE:
<223> OTHER INFORMATION: mLif Upstream Primer
```

-continued

```
<400> SEQUENCE: 13
gagtccagcc cataatgaag gt                                                  22

<210> SEQ ID NO 14
<211> LENGTH: 22
<212> TYPE: DNA
<213> ORGANISM: Artificial
<220> FEATURE:
<223> OTHER INFORMATION: mLif Downstream Primer

<400> SEQUENCE: 14
gtgcagaacc agcagcagta ag                                                  22

<210> SEQ ID NO 15
<211> LENGTH: 24
<212> TYPE: DNA
<213> ORGANISM: Artificial
<220> FEATURE:
<223> OTHER INFORMATION: mMMP-12 Upstream Primer

<400> SEQUENCE: 15
tggtattcaa ggagatgcac attt                                                24

<210> SEQ ID NO 16
<211> LENGTH: 25
<212> TYPE: DNA
<213> ORGANISM: Artificial
<220> FEATURE:
<223> OTHER INFORMATION: mMMP-12 Downstream Primer

<400> SEQUENCE: 16
ggtttgtgcc ttgaaaactt ttagt                                               25

<210> SEQ ID NO 17
<211> LENGTH: 21
<212> TYPE: DNA
<213> ORGANISM: Artificial
<220> FEATURE:
<223> OTHER INFORMATION: mTNFsf9 Upstream Primer

<400> SEQUENCE: 17
cgccaagcta ctggctaaaa a                                                   21

<210> SEQ ID NO 18
<211> LENGTH: 21
<212> TYPE: DNA
<213> ORGANISM: Artificial
<220> FEATURE:
<223> OTHER INFORMATION: mTNFsf9 Downstream Primer

<400> SEQUENCE: 18
ggctgtgcca gttcagagtt g                                                   21

<210> SEQ ID NO 19
<211> LENGTH: 21
<212> TYPE: DNA
<213> ORGANISM: Artificial
<220> FEATURE:
<223> OTHER INFORMATION: mVEGF Upstream Primer

<400> SEQUENCE: 19
cccacgtcag agagcaacat c                                                   21

<210> SEQ ID NO 20
```

```
<211> LENGTH: 21
<212> TYPE: DNA
<213> ORGANISM: Artificial
<220> FEATURE:
<223> OTHER INFORMATION: mVEFG Downstream Primer

<400> SEQUENCE: 20
tggctttggt gaggtttgat c                                               21
```